(12) United States Patent
Ruffing et al.

(10) Patent No.: US 11,834,650 B1
(45) Date of Patent: Dec. 5, 2023

(54) METHODS OF TRANSFECTION USING SONOPORATION

(71) Applicant: National Technology & Engineering Solutions of Sandia, LLC, Albuquerque, NM (US)

(72) Inventors: Anne Ruffing, Albuquerque, NM (US); Darren W. Branch, Albuquerque, NM (US); Ronald P. Manginell, Albuquerque, NM (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 805 days.

(21) Appl. No.: 16/446,971

(22) Filed: Jun. 20, 2019

Related U.S. Application Data

(60) Provisional application No. 62/689,003, filed on Jun. 22, 2018.

(51) Int. Cl.
*C12N 15/87* (2006.01)
*C12N 13/00* (2006.01)
*C12M 1/42* (2006.01)

(52) U.S. Cl.
CPC .............. *C12N 13/00* (2013.01); *C12M 35/04* (2013.01); *C12N 15/87* (2013.01)

(58) Field of Classification Search
CPC ......... C12N 13/00; C12N 15/87; C12M 35/04
See application file for complete search history.

(56) References Cited

U.S. PATENT DOCUMENTS

| | | |
|---|---|---|
| 5,820,922 A | 10/1998 | Ricco et al. |
| 5,834,627 A | 11/1998 | Ricco et al. |
| 6,096,656 A | 8/2000 | Matzke et al. |
| 6,171,378 B1 | 1/2001 | Manginell et al. |
| 6,224,728 B1 | 5/2001 | Oborny et al. |
| 6,527,835 B1 | 3/2003 | Manginell et al. |
| 6,627,421 B1 * | 9/2003 | Unger ............. C12M 35/04 204/600 |
| 6,666,907 B1 | 12/2003 | Manginell et al. |
| 6,699,392 B1 | 3/2004 | Manginell et al. |
| 6,772,513 B1 | 8/2004 | Frye-Mason et al. |
| 6,786,716 B1 | 9/2004 | Gardner et al. |
| 6,902,701 B1 | 6/2005 | Hughes et al. |
| 6,930,051 B1 | 8/2005 | Manginell et al. |
| 7,078,237 B1 | 7/2006 | Mowry et al. |
| 7,105,098 B1 | 9/2006 | Shul et al. |
| 7,118,712 B1 | 10/2006 | Manginell et al. |

(Continued)

OTHER PUBLICATIONS

Pdf document "dB vs dBm" is a webpage from Fluke Networks at https://www.flukenetworks.com/knowledge-base/dsp-fta-series/db-vs-dbm, accessed Feb. 10, 2022, publically available Aug. 5, 2015 according to Google (see p. 1) (Year: 2015).*

(Continued)

*Primary Examiner* — David W Berke-Schlessel
*Assistant Examiner* — Trent R Clarke
(74) *Attorney, Agent, or Firm* — Helen S. Baca; Samantha Updegraff

(57) ABSTRACT

The present invention relates to methods of transforming a cell by use of an acoustic transducer. In particular embodiments, the radiofrequency signal to the transducer can be tuned to provide optimal membrane disruption of the cell; and an agent, such as a nucleic acid, can then be delivered to the cell.

19 Claims, 9 Drawing Sheets

Specification includes a Sequence Listing.

(56) References Cited

U.S. PATENT DOCUMENTS

| | | |
|---|---|---|
| 7,168,298 B1 | 1/2007 | Manginell et al. |
| 7,399,449 B1 | 7/2008 | Oborny et al. |
| 7,422,724 B1 | 9/2008 | Manginell et al. |
| 7,708,943 B1 | 5/2010 | Robinson et al. |
| 7,727,314 B1 | 6/2010 | Manginell et al. |
| 7,799,280 B1 | 9/2010 | Manginell et al. |
| 7,878,063 B1 | 2/2011 | Cular et al. |
| 7,913,534 B1 | 3/2011 | Robinson et al. |
| 7,942,568 B1 | 5/2011 | Branch et al. |
| 8,119,859 B2 | 2/2012 | Vick et al. |
| 8,298,488 B1 | 10/2012 | Lewis et al. |
| 8,425,749 B1 | 4/2013 | Ravula et al. |
| 8,436,509 B1 | 5/2013 | Branch |
| 8,486,710 B2 | 7/2013 | Antel et al. |
| 8,525,619 B1 | 9/2013 | Olsson et al. |
| 8,669,688 B1 | 3/2014 | Branch |
| 8,709,791 B2 | 4/2014 | Larson et al. |
| 8,736,000 B1 | 5/2014 | Manginell et al. |
| 8,759,615 B2 | 6/2014 | Vick et al. |
| 9,096,823 B1 | 8/2015 | Branch et al. |
| 9,276,557 B1 | 3/2016 | Nordquist et al. |
| 9,337,800 B1 | 5/2016 | Olsson, III et al. |
| 9,472,689 B1 | 10/2016 | Elizondo-Decanini et al. |
| 9,512,421 B1 | 12/2016 | Branch et al. |
| 9,996,411 B1 | 6/2018 | Moorman et al. |
| 10,009,002 B1 | 6/2018 | Branch et al. |
| 10,031,135 B2 | 7/2018 | Larson et al. |
| 10,151,732 B1 | 12/2018 | Moorman et al. |
| 10,161,836 B2 | 12/2018 | Moorman et al. |
| 10,197,532 B1 | 2/2019 | Manginell et al. |
| 10,261,078 B2 | 4/2019 | Branch et al. |
| 2009/0317857 A1 | 12/2009 | Vick et al. |
| 2009/0317904 A1 | 12/2009 | Vick et al. |
| 2012/0208279 A1 | 8/2012 | Vick et al. |
| 2013/0078716 A1 | 3/2013 | Vick et al. |
| 2013/0295665 A1 | 11/2013 | Kilian et al. |
| 2015/0093830 A1 | 4/2015 | Vick et al. |
| 2015/0125960 A1* | 5/2015 | Liaw ............ C12N 15/8207 435/471 |
| 2019/0381507 A1* | 12/2019 | Weiss ............ B01L 3/502761 |

OTHER PUBLICATIONS

Pablo Guimarães, João S. Yunes, Mariana Silvia Cretoiu and Lucas J. Stal, Growth Characteristics of an Estuarine Heterocystous Cyanobacterium, 2017, Frontiers in Microbiology, vol. 8, Article 1132, pp. 1-13 (Year: 2017).*

U.S. Appl. No. 15/415,875, filed Jan. 25, 2017, Branch et al.

Adams, JD et al., "Integrated acoustic and magnetic separation in microfluidic channels," *Appl. Phys. Lett.* Dec. 21, 2009;95(25):254103 (3 pp.).

Adams., JD et al., "Tunable acoustophoretic band-pass particle sorter," *Appl. Phys. Lett.* Aug. 9, 2010;97(6):064103 (3 pp.).

Al Y et al., "Separation of *Escherichia coli* bacteria from peripheral blood mononuclear cells using standing surface acoustic waves," *Anal. Chem.* 2013;85(19):9126-34.

Azencott HR et al., "Influence of the cell wall on intracellular delivery to algal cells by electroporation and sonication," *Ultrasound Med. Biol.* 2007;33(11):1805-17.

Branch DW et al., "Intelligent front-end sample preparation tool using acoustic streaming," *Sandia Report No. SAND2009-6193*, Sep. 2009 (70 pp.).

Branch DW et al., "Nucleic acid extraction using a rapid, chemical free, ultrasonic technique for point-of-care diagnostics," *IEEE International Ultrasonics Symposium Proceedings*, held on Sep. 3-6, 2014, pp. 501-506.

Branch DW et al., "Rapid nucleic acid extraction and purification using a miniature ultrasonic technique," *Micromachines* 2017;8:228 (17 pp.).

Dehghani J et al., "Efficient and stable transformation of *Dunallella pseudosalina* by 3 strains of *Agrobacterium turnefaciens*," *Bioimpacts* 2017;7(4):247-54.

Delorme E, "Transformation of *Saccharomyces cerevisias* by electroporation." *Appl. Environ. Microbiol.* 1989;55(9):2242-6.

Jung B et al., "Acoustic particle filter with adjustable effective pore size for automated sample preparation," *Anal. Chem.* 2008;80(22):8447-52.

Kilian O et al., "High efficiency homologous mecombination in the oil-producing alga *Nannochloropsis* sp.," *Proc. Nat'l Acad Sci USA* 2011;108(52):21265-9.

Kira N et al., "Nuclear transformation of the diatom *Phaeodactylum tricomufum* using PCR-amplified DNA fragments by microparticle bombardment," *Mar. Genomics* 2016;25:49-56.

Ma F et al., "Biodiesel production: a review,"*Bioresource Technol.* 1999;70:1-15.

Ortiz-Matamoros MF et al., "Genetic transformation of cell-walled plant and algae cells: delivering DNA through the cell wall,"*Brief Funct. Genomics* 2018;17(1):26-33.

Pratheesh PT et al., "An efficient protocol for the *Agrobacterium*-mediated genetic transformation of microalga *Chlamydomonas reinhardhi*,"*Mot. Biotechnol.* 2014;56(8):507-15.

Ravula SK et al., "A microfluidic system combining acoustic and dielectrophoretic particle preconcentration and focusing," *Sens. Actuat. B* 2008;130:645-52.

Schneider RCS et al., "Potential production of biofuel from microalgae biomass produced in wastewater, " in *Biodiesel—Feedstocks, Production and Applications*. Prof. Zhen Fang (ed.); InTech, 2012, 22 pp.

Shi J et al., "Continuous particle separation in a microfluidic channel via standing surface: acoustic waves (SSAW)" *Lab Chip* 2009;9(23):3354-9.

Shung KK et al., "Piezoelectric materials for high frequency medical imaging applications: a review," *J. Electroceram.* 2007;19:139-45.

Tran NH et al., "Catalytic upgrading of biorefinery oil from microalgae," *Fuels* 2010:89:265-74.

Wan M et al., "An improved colony PCR procedure for genetic screening of *Chlorella* and related microalgae," *Biotechol. Lett.* 2011; 33(8):1615-9.

Wildschut J et al., "Catalyst studies on the hydrotreatment of fast pyrolysis oil." *Appl. Catalysis B* 2010;99:298-306.

Wu X et al., "Ultrasound-mediated intracellular delivery of fluorescent dyes and DNA into microalgal cells." *Algal Res.* 2016;15:210-6.

Yang ANJ et al., "Acoustophoretic sorting of viable mammalian cells in a microfluidic device," *Anal. Chem.* 2012;84(24):10756-62.

Yeo LY et al., "Surface acoustic wave microfluidics," *Annu. Rev. Fluid Mech* 2014;46:379-406.

Yeo LY et al., "Ultrafast microfluidics using surface acoustic wave," *Biomicrofluidics* 2009;3(1):12002 (23 pp.).

* cited by examiner

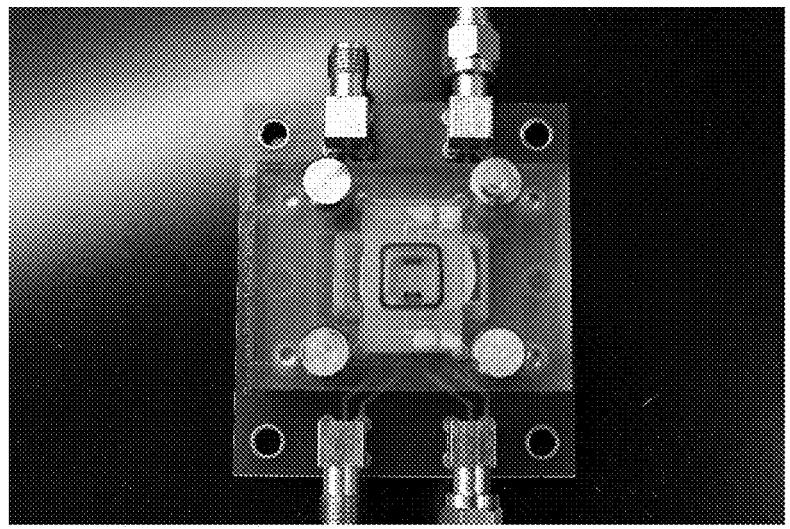

FIG. 2

```
   1 gcactttcg gggaaatgtg cgcggaaccc ctatttgttt attttctaa atacattcaa
  61 atatgtatcc gctcatgaga caataaccct gataaatgct tcaataatat tgaaaaagga
 121 agagtatgag tattcaacat ttccgtgtcg cccttattcc cttttttgcg gcattttgcc
 181 ttcctgtttt tgctcaccca gaaacgctgg tgaaagtaaa agatgctgaa gatcagttgg
 241 gtgcacgagt gggttacatc gaactggatc tcaacagcgg taagatcctt gagagttttc
 301 gccccgaaga acgttttcca atgatgagca cttttaaagt tctgctatgt ggcgcggtat
 361 tatcccgtat tgacgccggg caagagcaac tcggtcgccg catacactat tctcagaatg
 421 acttggttga gtactcacca gtcacagaaa agcatcttac ggatggcatg acagtaagag
 481 aattatgcag tgctgccata accatgagtg ataacactgc ggccaactta cttctgacaa
 541 cgatcggagg accgaaggag ctaaccgctt ttttgcacaa catgggggat catgtaactc
 601 gccttgatcg ttgggaaccg gagctgaatg aagccatacc aaacgacgag cgtgacacca
 661 cgatgcctgt agcaatggca acaacgttgc gcaaactatt aactggcgaa ctacttactc
 721 tagcttcccg gcaacaatta atagactgga tggaggcgga taaagttgca ggaccacttc
 781 tgcgctcggc ccttccggct ggctggttta ttgctgataa atctggagcc ggtgagcgtg
 841 ggtctcgcgg tatcattgca gcactggggc cagatggtaa gccctcccgt atcgtagtta
 901 tctacacgac ggggagtcag gcaactatgg atgaacgaaa tagacagatc gctgagatag
 961 gtgcctcact gattaagcat tggtaactgt cagaccaagt ttactcatat atactttaga
1021 ttgatttaaa acttcatttt taatttaaaa ggatctaggt gaagatcctt tttgataatc
1081 tcatgaccaa aatcccttaa cgtgagtttt cgttccactg agcgtcagac cccgtagaaa
1141 agatcaaagg atcttcttga tccttttt ttctgcgcgt aatctgctgc ttgcaaacaa
1201 aaaaaccacc gctaccagcg gtggtttgtt tgccggatca agagctacca actctttttc
1261 cgaaggtaac tggcttcagc agagcgcaga taccaaatac tgtccttcta gtgtagccgt
1321 agttaggcca ccacttcaag aactctgtag caccgcctac atacctcgct ctgctaatcc
1381 tgttaccagt ggctgctgcc agtggcgata agtcgtgtct taccgggttg gactcaagac
1441 gatagttacc ggataaggcg cagcggtcgg gctgaacggg gggttcgtgc acacagccca
1501 gcttggagcg aacgacctac accgaactga gatacctaca gcgtgagcta tgagaaagcg
1561 ccacgcttcc cgaagggaga aaggcggaca ggtatccggt aagcggcagg gtcggaacag
1621 gagagcgcac gagggagctt ccaggggaa acgcctggta tctttatagt cctgtcgggt
1681 ttcgccacct ctgacttgag cgtcgatttt tgtgatgctc gtcaggggg cggagcctat
1741 ggaaaaacgc cagcaacgcg gccttttac ggttcctggc cttttgctgg ccttttgctc
1801 acatgttctt tcctgcgtta tccctgatt ctgtggataa ccgtattacc gcctttgagt
1861 gagctgatac cgctcgccgc agccgaacga ccgagcgcag cgagtcagtg agcgaggaag
```

FIG. 3A

```
1921 cggaagagcg cccaatacgc aaaccgcctc tccccgcgcg ttggccgatt cattaatgca
1981 gctggcacga caggtttccc gactggaaag cgggcagtga gcgcaacgca attaatgtga
2041 gttagctcac tcattaggca ccccaggctt tacactttat gcttccggct cgtatgttgt
2101 gtggaattgt gagcggataa caatttcaca caggaaacag ctatgaccat gattacgcca
2161 agctcgaaat taaccctcac taagggaac aaaagctgct agcatgcgcc cacgttcttt
2221 tacccctgta cacgcttctg tttgttactt ctgctctgtc gttctttatt ccgcatgct
2281 tgctaactgt ctatatacct tgtatgagcg tgcgcgacaa ggttgatagg attaggactg
2341 gcccctgtct ttgttctgtt cattcttaac gccactcggg acgtgtttcg ggcgactcat
2401 tgacctggtg tgcgatctta tttttgattt tctgtagccc tcttaaatgt ttttccatga
2461 gaaattatac acctgaagat catcgtccat ctcgttcggc acactttctc tagcgacctt
2521 gtgtgtacgc gaatgcgtgt ccgggatatc gcatgcttgt ttcaccttac accctggtcc
2581 atgattgaaa tgtcaagatt ttggttcatc taggacggct ctaccttata tctcacgaga
2641 acaaccacaa ctcacatctg tcaacagaag tctccacttt aaaacttttc tcataataat
2701 ggccaagctc acttcggccg ttcctgtcct cacggctcgc gacgtcgccg gtgccgtgga
2761 attttggact gaccgcctcg gatttcccg tgactttgtc gaagatgact tcgccggcgt
2821 cgttcgtgat gatgttacgc tcttcatcag tgccgttcaa gaccaagtcg tccccgataa
2881 cactttggcc tgggtctggg tccgcggatt ggacgagctt tatgccgagt ggtccgaagt
2941 ggtctccacc aactttcgcg acgcttcggg ccccgctatg actgaaattg gcgaacagcc
3001 ctggggtcgc gaattcgccc tccgtgaccc agctggcaac tgcgtccatt tcgtcgccga
3061 ggaacaggat taagtggccc tagaggcagc gccgtcgctt ggcagccgcg actggctcgt
3121 gcgcggggcg tgggggggcc gggttccttc gcttccggaa agggttcggg gggtgacgag
3181 agctgctggg ggccatcggg tcgagatgac cctagtcttt cggagcactc ggtacccac
3241 cagccccgga gagagggaag gagggaggtg gacccgcggg gagacccgt gcttctggtc
3301 gtgcccgggc agggcgtgtg tgtgtaggtt tgattctgtt ttttttgtc gacgtgaccg
3361 cctcggggtc ctctcactcg tctccctttt gggaaggccg cgtcgctctc agtcccaatt
3421 cgccctatag tgagtcgtat tacaattcac tggccgtcgt tttacaacgt cgtgactggg
3481 aaaaccctgg cgttacccaa cttaatcgcc ttgcagcaca tccccctttc gccagctggc
3541 gtaatagcga agaggcccgc accgatcgcc cttcccaaca gttgcgcagc ctgaatggcg
3601 aatggaaatt gtaagcgtta atattttgtt aaaattcgcg ttaaattttt gttaaatcag
3661 ctcattttttt aaccaatagg ccgaaatcgg caaaatccct tataaatcaa agaatagac
3721 cgagataggg ttgagtgttg ttccagtttg gaacaagagt ccactattaa agaacgtgga
3781 ctccaacgtc aaagggcgaa aaaccgtcta tcagggcgat ggcccactac gtgaaccatc
3841 accctaatca agttttttgg ggtcgaggtg ccgtaaagca ctaaatcgga accctaaagg
3901 gagccccga tttagagctt gacggggaaa gccggcgaac gtggcgagaa aggaagggaa
3961 gaaagcgaaa ggagcgggcg ctagggcgct ggcaagtgta gcggtcacgc tgcgcgtaac
4021 caccacaccc gccgcgctta atgcgccgct acagggcgcg tcaggtg
```

FIG. 3B

$\theta_R = \sin^{-1}(V_{fluid}/V_{R,Air})$  $\theta_R = 23°$

US 11,834,650 B1

SEQUENCE LISTING

<160> NUMBER OF SEQ ID NOS: 1

<210> SEQ ID NO 1
<211> LENGTH: 4067
<212> TYPE: DNA
<213> ORGANISM: Artificial Sequence
<220> FEATURE:
<223> OTHER INFORMATION: Synthetic pble-vcp DNA construct

<400> SEQUENCE: 1

```
gcacttttcg gggaaatgtg cgcggaaccc ctatttgttt attttctaa atacattcaa      60 atatgtatcc gctcatgaga caataaccct gataaatgct tcaataatat tgaaaaagga     120
agagtatgag tattcaacat ttccgtgtcg cccttattcc cttttttgcg gcattttgcc    180
ttcctgtttt tgctcaccca gaaacgctgg tgaaagtaaa agatgctgaa gatcagttgg     240
gtgcacgagt gggttacatc gaactggatc tcaacagcgg taagatcctt gagagttttc     300
gccccgaaga acgttttcca atgatgagca cttttaaagt tctgctatgt ggcgcggtat    360
tatcccgtat tgacgccggg caagagcaac tcggtcgccg catacactat tctcagaatg    420
acttggttga gtactcacca gtcacagaaa agcatcttac ggatggcatg acagtaagag     480
aattatgcag tgctgccata accatgagtg ataacactgc ggccaactta cttctgacaa     540
cgatcggagg accgaaggag ctaaccgctt ttttgcacaa catgggggat catgtaactc     600
gccttgatcg ttgggaaccg gagctgaatg aagccatacc aaacgacgag cgtgacacca    660
cgatgcctgt agcaatggca acaacgttgc gcaaactatt aactggcgaa ctacttactc     720
tagcttcccg gcaacaatta atagactgga tggaggcgga taaagttgca ggaccacttc    780
tgcgctcggc ccttccggct ggctggttta ttgctgataa atctggagcc ggtgagcgtg     840
ggtctcgcgg tatcattgca gcactggggc cagatggtaa gccctcccgt atcgtagtta     900
tctacacgac ggggagtcag gcaactatgg atgaacgaaa tagacagatc gctgagatag     960
gtgcctcact gattaagcat tggtaactgt cagaccaagt ttactcatat atactttaga    1020
ttgatttaaa acttcatttt taatttaaaa ggatctaggt gaagatcctt tttgataatc    1080
tcatgaccaa aatcccttaa cgtgagtttt cgttccactg agcgtcagac cccgtagaaa    1140
```

```
agatcaaagg atcttcttga gatccttttt ttctgcgcgt aatctgctgc ttgcaaacaa    1200
aaaaaccacc gctaccagcg gtggtttgtt tgccggatca agagctacca actcttttc     1260 cgaaggtaac tggcttcagc agagcgcaga taccaaatac tgtccttcta gtgtagccgt    1320
agttaggcca ccacttcaag aactctgtag caccgcctac atacctcgct ctgctaatcc    1380
tgttaccagt ggctgctgcc agtggcgata agtcgtgtct taccggggttg gactcaagac   1440 gatagttacc ggataaggcg cagcggtcgg gctgaacggg gggttcgtgc acacagccca    1500
gcttggagcg aacgacctac accgaactga gatacctaca gcgtgagcta tgagaaagcg    1560
ccacgcttcc cgaagggaga aaggcggaca ggtatccggt aagcggcagg gtcggaacag    1620
gagagcgcac gagggagctt ccaggggggaa acgcctggta tctttatagt cctgtcgggt   1680
ttcgccacct ctgacttgag cgtcgatttt tgtgatgctc gtcagggggg cggagcctat    1740
ggaaaaacgc cagcaacgcg gccttttac ggttcctggc cttttgctgg ccttttgctc     1800
acatgttctt tcctgcgtta tccctgatt ctgtggataa ccgtattacc gcctttgagt     1860
gagctgatac cgctcgccgc agccgaacga ccgagcgcag cgagtcagtg agcgaggaag    1920
cggaagagcg cccaatacgc aaaccgcctc tccccgcgcg ttggccgatt cattaatgca    1980
gctggcacga caggtttccc gactggaaag cgggcagtga gcgcaacgca attaatgtga    2040
gttagctcac tcattaggca ccccaggctt tacactttat gcttccggct cgtatgttgt    2100
gtggaattgt gagcggataa caattcaca caggaaacag ctatgaccat gattacgcca     2160
agctcgaaat taaccctcac taaagggaac aaaagctgct agcatgcgcc cacgttcttt    2220 taccctgta cacgcttctg tttgttactt ctgctctgtc gttctttatt tccgcatgct     2280
tgctaactgt ctatatacct tgtatgagcg tgcgcgacaa ggttgatagg attaggactg    2340 gccctgtct ttgttctgtt cattcttaac gccactcggg acgtgtttcg ggcgactcat     2400
tgacctggtg tgcgatctta ttttgattt tctgtagccc tcttaaatgt ttttccatga     2460
gaaattatac acctgaagat catcgtccat ctcgttcggc acactttctc tagcgacctt    2520
gtgtgtacgc gaatgcgtgt ccgggatatc gcatgcttgt ttcaccttac accctggtcc    2580
atgattgaaa tgtcaagatt ttggttcatc taggacggct ctaccttata tctcacgaga    2640
acaaccacaa ctcacatctg tcaacagaag tctccacttt aaaacttttc tcataataat    2700
ggccaagctc acttcggccg ttcctgtcct cacggctcgc gacgtcgccg gtgccgtgga    2760
attttggact gaccgcctcg gattttcccg tgactttgtc gaagatgact tcgccggcgt    2820
cgttcgtgat gatgttacgc tcttcatcag tgccgttcaa gaccaagtcg tccccgataa    2880
cactttggcc tgggtctggg tccgcggatt ggacgagctt tatgccgagt ggtccgaagt    2940
ggtctccacc aactttcgcg acgcttcggg ccccgctatg actgaaattg gcgaacagcc    3000
ctggggtcgc gaattcgccc tccgtgaccc agctggcaac tgcgtccatt tcgtcgccga    3060
ggaacaggat taagtggccc tagaggcagc gccgtcgctt ggcagccgcg actggctcgt    3120
gcgcggggcg tgggggggcc gggttccttc gcttccggaa agggttcggg gggtgacgag    3180
agctgctggg ggccatcggg tcgagatgac cctagtcttt cggagcactc ggtaccccac    3240
cagccccgga gagagggaag gagggaggtg gaccgcgggg gagacccgt gcttctggtc     3300 gtgcccgggc agggcgtgtg tgtgtaggtt tgattctgtt ttttttttgtc gacgtgaccg    3360 cctcggggtc ctctcactcg tctcccttt gggaaggccg cgtcgctctc agtcccaatt     3420 cgcccctatag tgagtcgtat tacaattcac tggccgtcgt tttacaacgt cgtgactggg   3480
```

| | | | | | |
|---|---|---|---|---|---|
| aaaaccctgg | cgttacccaa | cttaatcgcc | ttgcagcaca | tcccccttc | gccagctggc | 3540
| gtaatagcga | agaggcccgc | accgatcgcc | cttcccaaca | gttgcgcagc | ctgaatggcg | 3600
| aatggaaatt | gtaagcgtta | atattttgtt | aaaattcgcg | ttaaattttt | gttaaatcag | 3660
| ctcattttt | aaccaatagg | ccgaaatcgg | caaaatccct | tataaatcaa | aagaatagac | 3720
| cgagataggg | ttgagtgttg | ttccagtttg | gaacaagagt | ccactattaa | agaacgtgga | 3780
| ctccaacgtc | aaagggcgaa | aaaccgtcta | tcagggcgat | ggcccactac | gtgaaccatc | 3840
| accctaatca | agtttttgg | ggtcgaggtg | ccgtaaagca | ctaaatcgga | accctaaagg | 3900
| gagcccccga | tttagagctt | gacggggaaa | gccggcgaac | gtggcgagaa | aggaagggaa | 3960
| gaaagcgaaa | ggagcgggcg | ctagggcgct | ggcaagtgta | gcggtcacgc | tgcgcgtaac | 4020
| caccacaccc | gccgcgctta | atgcgccgct | acagggcgcg | tcaggtg | | 4067

METHODS OF TRANSFECTION USING SONOPORATION

CROSS-REFERENCE TO RELATED APPLICATION

This application claims the benefit of U.S. Provisional Application No. 62/689,003, filed Jun. 22, 2018, which is hereby incorporated by reference in its entirety.

STATEMENT OF GOVERNMENT INTEREST

This invention was made with Government support under Contract No. DE-NA0003525 awarded by the United States Department of Energy/National Nuclear Security Administration. The Government has certain rights in the invention.

REFERENCE TO A SEQUENCE LISTING APPENDIX

A sequence listing appendix including an ASCII formatted file accompanies this application. The appendix includes a file named "SD14531_1_ST25.txt," created on Jun. 17, 2019 (size of 5.66 kilobytes), which is hereby incorporated by reference in its entirety.

FIELD OF THE INVENTION

The present invention relates to methods of transforming a cell by use of an acoustic transducer. In particular embodiments, the radiofrequency signal to the transducer can be tuned to provide optimal membrane disruption of the cell; and an agent, such as a nucleic acid, can then be delivered to the cell.

BACKGROUND OF THE INVENTION

Delivery of agents to cells, such as microorganisms, can be challenging. For instance, transfection, or delivery of nucleic acid, into microorganisms can impeded by cell walls that prevent uptake. Conventional methods of transfection include electroporation, which can have limited success in certain cell types. Accordingly, there is a need for improved methods for delivering agents to provide transformed cells.

SUMMARY OF THE INVENTION

The present invention relates, in part, to the use of acoustic waves to deliver an agent (e.g., a nucleic acid) to a cell (e.g., a microorganism). In one non-limiting instance, delivery of nucleic acid (e.g., DNA) into microorganisms can be challenging due to cell wall barriers that prevent uptake. Acoustic-based delivery (i.e., sonoporation) of such an agent can be an effective approach for transfection of microorganisms that cannot be modified using conventional approaches, such as electroporation. Exemplary acoustic-based devices include, e.g., surface acoustic wave (SAW) platforms and bulk acoustic wave (BAW) platforms. Described herein are methods of employing such platforms to deliver agents to microorganisms that are difficult to transfect or transform, including but not limited to eukaryotic algae, Gram-positive bacteria, and Gram-negative bacteria. Additional details follow.

Definitions

As used herein, the term "about" means+/−10% of any recited value. As used herein, this term modifies any recited value, range of values, or endpoints of one or more ranges.

By "disposed" is meant that a first structure is located in a particular position relative to a second structure. This position includes direct contact between the first and second structures (e.g., direct continuous or noncontinuous contact) or indirect contact between the first and second structures (e.g., by way of third or further structure(s) disposed between the first and second structures).

By "fluidic communication," as used herein, refers to any duct, channel, tube, pipe, chamber, or pathway through which a substance, such as a liquid, gas, or solid may pass substantially unrestricted when the pathway is open. When the pathway is closed, the substance is substantially restricted from passing through. Typically, limited diffusion of a substance through the material of a cartridge, platform, platen, layer (e.g., thermal exchange layer or any layer described herein), and/or a substrate, which may or may not occur depending on the compositions of the substance and materials, does not constitute fluidic communication.

By "microfluidic" or "micro" is meant having at least one dimension that is less than 1 mm and, optionally, equal to or larger than about 1 µm. For instance, a microstructure (e.g., any structure described herein, such as a microfluidic channel) can have a length, width, height, cross-sectional dimension, circumference, radius (e.g., external or internal radius), or diameter that is less than 1 mm.

By "nanofluidic" or "nano" is meant having at least one dimension that is less than 1 m but equal to or larger than about 1 nm. For instance, a nanostructure (e.g., any structure described herein, such as a nanofluidic channel) can have a length, width, height, cross-sectional dimension, circumference, radius (e.g., external or internal radius), or diameter that is less than 1 m but equal to or larger than 1 nm. In other instances, the nanostructure has a dimension that is of from about 1 nm to about 1 µm.

The term "agent" is used herein to describe any molecule or compound, which can be transfected or delivered according to the present invention. Non-limiting exemplary agents may include, for example, a nucleic acid (e.g., RNA, such as mRNA, siRNA, shRNA, and micro RNA; or DNA, such as double stranded or linear DNA, complementary DNA (cDNA), minicircle DNA, naked DNA and plasmid DNA, which optionally may be supercoiled and/or packaged (e.g., with histones)), a polypeptide (e.g., a protein), a small molecule bioactive agent, a vector, an expression cassette, etc. Agents may also include a reporter as described herein.

The term "effective" is used herein, unless otherwise indicated, to describe an amount of an agent, compound, composition or component which, when used within the context of its use, produces or effects an intended result. The term effective subsumes all other effective amount or effective concentration terms (including the term "therapeutically effective") which are otherwise described or used in the present application.

The terms "polynucleotide" and "nucleic acid," used interchangeably herein, refer to a polymeric form of nucleotides of any length, either ribonucleotides or deoxyribonucleotides. Thus, this term includes, but is not limited to, single-stranded (e.g., sense or antisense), double-stranded, or multi-stranded ribonucleic acids (RNAs), deoxyribonucleic acids (DNAs), threose nucleic acids (TNAs), glycol nucleic acids (GNAs), peptide nucleic acids (PNAs), locked nucleic acids (LNAs), or hybrids thereof, genomic DNA, cDNA, DNA-RNA hybrids, or a polymer comprising purine and pyrimidine bases or other natural, chemically or biochemically modified, non-natural, or derivatized nucleotide bases. Polynucleotides can have any useful two-dimensional or three-dimensional structure or motif, such as regions including one or more duplex, triplex, quadruplex, hairpin, and/or pseudoknot structures or motifs.

The term "modified," as used in reference to nucleic acids, means a nucleic acid sequence including one or more modifications to the nucleobase, nucleoside, nucleotide, phosphate group, sugar group, and/or internucleoside linkage (e.g., phosphodiester backbone, linking phosphate, or a phosphodiester linkage).

The nucleoside modification may include, but is not limited to, pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-methoxy-2-thio-pseudouridine, 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl) adenosine, 2-methylthio-N6-(cis-hydroxyisopentenyl) adenosine, N6-glycinylcarbamoyl adenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine, inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methyl-guanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine, and combinations thereof.

A sugar modification may include, but is not limited to, a locked nucleic acid (LNA, in which the 2'-hydroxyl is connected by a $C_{1-6}$ alkylene or $C_{1-6}$ heteroalkylene bridge to the 4'-carbon of the same ribose sugar), replacement of the oxygen in ribose (e.g., with S, Se, or alkylene, such as methylene or ethylene), addition of a double bond (e.g., to replace ribose with cyclopentenyl or cyclohexenyl), ring contraction of ribose (e.g., to form a 4-membered ring of cyclobutane or oxetane), ring expansion of ribose (e.g., to form a 6- or 7-membered ring having an additional carbon or heteroatom, such as for anhydrohexitol, altritol, mannitol, cyclohexanyl, cyclohexenyl, and morpholino that also has a phosphoramidate backbone), multicyclic forms (e.g., tricyclic), and "unlocked" forms, such as glycol nucleic acid (GNA) (e.g., R-GNA or S-GNA, where ribose is replaced by glycol units attached to phosphodiester bonds), threose nucleic acid (TNA, where ribose is replace with a-L-threo-furanosyl-(3'→2')), and peptide nucleic acid (PNA, where 2-amino-ethyl-glycine linkages replace the ribose and phosphodiester backbone). The sugar group can also contain one or more carbons that possess the opposite stereochemical configuration than that of the corresponding carbon in ribose. Thus, a polynucleotide molecule can include nucleotides containing, e.g., arabinose, as the sugar.

A backbone modification may include, but is not limited to, 2'-deoxy- or 2'-O-methyl modifications. A phosphate group modification may include, but is not limited to, phosphorothioate, phosphoroselenates, boranophosphates, boranophosphate esters, hydrogen phosphonates, phosphoramidates, phosphorodiamidates, alkyl or aryl phosphonates, phosphotriesters, phosphorodithioates, bridged phosphoramidates, bridged phosphorothioates, or bridged methylene-phosphonates.

"Complementarity" or "complementary" refers to the ability of a nucleic acid to form hydrogen bond(s) with another nucleic acid sequence by either traditional Watson-Crick or other non-traditional types, e.g., form Watson-Crick base pairs and/or G/U base pairs, "anneal", or "hybridize," to another nucleic acid in a sequence-specific, antiparallel, manner (i.e., a nucleic acid specifically binds to a complementary nucleic acid) under the appropriate in vitro and/or in vivo conditions of temperature and solution ionic strength. As is known in the art, standard Watson-Crick base-pairing includes: adenine (A) pairing with thymidine (T), adenine (A) pairing with uracil (U), and guanine (G) pairing with cytosine (C). In addition, it is also known in the art that for hybridization between two RNA molecules (e.g., dsRNA), guanine (G) base pairs with uracil (U). A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" or "sufficient complementarity" as used herein refers to a degree of complementarity that is at least 60%, 65%, 70%, 75%, 80%, 85%, 90%, 95%. 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part 1, Second Chapter "Overview of principles of hybridization and the strategy of nucleic acid probe assay", Elsevier, N.Y.

"Hybridization" refers to a reaction in which one or more polynucleotides react to form a complex that is stabilized via hydrogen bonding between the bases of the nucleotide residues.

The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence. Hybridization and washing conditions are well known and exemplified in Sambrook J, Fritsch E F, and Maniatis T, "Molecular Cloning: A Laboratory Manual," Second Edition, Cold Spring Harbor Laboratory Press, Cold Spring Harbor (1989), particularly Chapter 11 and Table 11.1 therein; and Sambrook J and Russell W, "Molecular Cloning: A Laboratory Manual," Third Edition, Cold Spring Harbor Laboratory Press, Cold Spring Harbor (2001). The conditions of temperature and ionic strength determine the "stringency" of the hybridization.

Hybridization requires that the two nucleic acids contain complementary sequences, although mismatches between bases are possible. The conditions appropriate for hybridization between two nucleic acids depend on the length of the nucleic acids and the degree of complementation, variables well known in the art. The greater the degree of complementation between two nucleotide sequences, the greater the value of the melting temperature (Tm) for hybrids of nucleic acids having those sequences. For hybridizations between nucleic acids with short stretches of complementarity (e.g., complementarity over 35 or less, 30 or less, 25 or less, 22 or less, 20 or less, or 18 or less nucleotides) the position of mismatches becomes important (see Sambrook et al., supra, 11.7-11.8). Typically, the length for a hybridizable nucleic acid is at least about 10 nucleotides. Illustrative minimum lengths for a hybridizable nucleic acid are: at least about 15 nucleotides; at least about 20 nucleotides; at least about 22 nucleotides; at least about 25 nucleotides; and at least about 30 nucleotides). Furthermore, the skilled artisan will recognize that the temperature and wash solution salt concentration may be adjusted as necessary, according to factors such as length of the region of complementation and the degree of complementation.

It is understood in the art that the sequence of polynucleotide need not be 100% complementary to that of its target nucleic acid to be specifically hybridizable or hybridizable. Moreover, a polynucleotide may hybridize over one or more segments such that intervening or adjacent segments are not involved in the hybridization event (e.g., a loop structure or hairpin structure). A polynucleotide can comprise at least 70%, at least 80%, at least 90%, at least 95%, at least 99%, or 100% sequence complementarity to a target region within the target nucleic acid sequence to which they are targeted. For example, an antisense nucleic acid in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. Percent complementarity between particular stretches of nucleic acid sequences within nucleic acids can be determined routinely using BLAST programs (basic local alignment search tools) and PowerBLAST programs known in the art (Altschul S F et al., *J. Mol. Biol.* 1990; 215:403-10; Zhang J et al., *Genome Res.* 1997; 7:649-56) or by using the Gap program (Wisconsin Sequence Analysis Package, Version 8 for Unix, Genetics Computer Group, University Research Park, Madison Wis.), using default settings, which uses the algorithm of Smith T F et al., *Adv. Appl. Math.* 1981; 2(4):482-9).

By "protein," "peptide," or "polypeptide," as used interchangeably, is meant any chain of more than two amino acids, regardless of post-translational modification (e.g., glycosylation or phosphorylation), constituting all or part of a naturally occurring polypeptide or peptide, or constituting a non-naturally occurring polypeptide or peptide, which can include coded amino acids, non-coded amino acids, modified amino acids (e.g., chemically and/or biologically modified amino acids), and/or modified backbones.

The term "fragment" is meant a portion of a nucleic acid or a polypeptide that is at least one nucleotide or one amino acid shorter than the reference sequence. This portion contains, preferably, at least about 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, 1000, 1250, 1500, 1750, 1800 or more nucleotides; or 10, 20, 30, 40, 50, 60, 70, 80, 90, 100, 150, 200, 250, 300, 350, 400, 450, 500, 550, 600, 640 amino acids or more. In another example, any polypeptide fragment can include a stretch of at least about 5 (e.g., about 10, about 20, about 30, about 40, about 50, or about 100) amino acids that are at least about 40% (e.g., about 50%, about 60%, about 70%, about 80%, about 90%, about 95%, about 87%, about 98%, about 99%, or about 100%) identical to any of the sequences described herein can be utilized in accordance with the invention. In certain embodiments, a polypeptide to be utilized in accordance with the invention includes 2, 3, 4, 5, 6, 7, 8, 9, 10, or more mutations (e.g., one or more conservative amino acid substitutions, as described herein). In yet another example, any nucleic acid fragment can include a stretch of at least about 5 (e.g., about 7, about 8, about 10, about 12, about 14, about 18, about 20, about 24, about 28, about 30, or more) nucleotides that are at least about 40% (about 50%, about 60%, about 70%, about 80%, about 90%, about 95%, about 87%, about 98%, about 99%, or about 100%) identical to any of the sequences described herein can be utilized in accordance with the invention.

The term "conservative amino acid substitution" refers to the interchangeability in proteins of amino acid residues having similar side chains (e.g., of similar size, charge, and/or polarity). For example, a group of amino acids having aliphatic side chains consists of glycine, alanine, valine, leucine, and isoleucine; a group of amino acids having aliphatic-hydroxyl side chains consists of serine and threonine; a group of amino acids having amide containing side chains consisting of asparagine and glutamine; a group of amino acids having aromatic side chains consists of phenylalanine, tyrosine, and tryptophan; a group of amino acids having basic side chains consists of lysine, arginine, and histidine; a group of amino acids having acidic side chains consists of glutamic acid and aspartic acid; and a group of amino acids having sulfur containing side chains consists of cysteine and methionine. Exemplary conservative amino acid substitution groups are valine-leucine-isoleucine, phenylalanine-tyrosine, lysine-arginine, alanine-valine, glycine-serine, glutamate-aspartate, and asparagine-glutamine.

As used herein, when a polypeptide or nucleic acid sequence is referred to as having "at least X % sequence identity" to a reference sequence, it is meant that at least X percent of the amino acids or nucleotides in the polypeptide or nucleic acid are identical to those of the reference sequence when the sequences are optimally aligned. An optimal alignment of sequences can be determined in various ways that are within the skill in the art, for instance, the Smith Waterman alignment algorithm (Smith T F et al., *J. Mol. Biol.* 1981; 147:195-7) and BLAST (Basic Local Alignment Search Tool; Altschul S F et al., *J. Mol. Biol.* 1990; 215:403-10). These and other alignment algorithms are accessible using publicly available computer software such as "Best Fit" (Smith T F et al., *Adv. Appl. Math.* 1981; 2(4):482-9) as incorporated into GeneMatcher Plus™ (Schwarz and Dayhof, "Atlas of Protein Sequence and Structure," ed. Dayhoff, M. O., pp. 353-358, 1979), BLAST, BLAST-2, BLAST-P, BLAST-N, BLAST-X, WU-BLAST-2, ALIGN, ALIGN-2, CLUSTAL, T-COFFEE, MUSCLE, MAFFT, or Megalign (DNASTAR). In addition, those skilled in the art can determine appropriate parameters for measuring alignment, including any algorithms needed to achieve optimal alignment over the length of the sequences being compared. In general, for polypeptides, the length of comparison sequences can be at least five amino acids, preferably 10, 20, 30, 40, 50, 60, 70, 80, 90, 100, 125, 150, 175, 200, 250, 300, 400, 500, 600, 700, or more amino acids, up to the entire length of the polypeptide. For nucleic acids, the length of comparison sequences can generally be at least 10, 20, 30, 40, 50, 60, 70, 80, 90, 100, 125, 150, 175, 200, 250, 300, 400, 500, 600, 700, 800, 900, 1000, 1100, 1200, 1300, 1400, 1500, 1600, 1700, 1800, 1900, 2000, 2100, or more nucleotides, up to the entire length of the nucleic acid molecule. It is understood that for the purposes of determining sequence identity when comparing a DNA sequence to an RNA sequence, a thymine nucleotide is equivalent to a uracil nucleotide.

By "substantial identity" or "substantially identical" is meant a polypeptide or nucleic acid sequence that has the same polypeptide or nucleic acid sequence, respectively, as a reference sequence, or has a specified percentage of amino acid residues or nucleotides, respectively, that are the same at the corresponding location within a reference sequence when the two sequences are optimally aligned. For example, an amino acid sequence that is "substantially identical" to a reference sequence has at least about 50%, 60%, 70%, 75%, 80%, 85%, 90%, 95%, 96%, 97%, 98%, 99%, or 100% sequence identity to the reference amino acid sequence. For polypeptides, the length of comparison sequences will generally be at least 5, 6, 7, 8, 9, 10, 11, 12, 13, 14, 15, 16, 17, 18, 19, 20, 25, 50, 75, 90, 100, 150, 200, 250, 300, or 350 contiguous amino acids (e.g., a full-length sequence). For nucleic acids, the length of comparison sequences will generally be at least 5, 10, 11, 12, 13, 14, 15, 16, 17, 18, 19, 20, 21, 22, 23, 24, or 25 contiguous nucleotides (e.g., the full-length nucleotide sequence). Sequence identity may be measured using sequence analysis software on the default setting (e.g., Sequence Analysis Software Package of the Genetics Computer Group, University of Wisconsin Biotechnology Center, 1710 University Avenue, Madison, WI, 53705). Such software may match similar sequences by assigning degrees of homology to various substitutions, deletions, and other modifications.

The term "chimeric" as used herein as applied to a nucleic acid or polypeptide refers to two components that are defined by structures derived from different sources. For example, where "chimeric" is used in the context of a chimeric polypeptide, the chimeric polypeptide includes amino acid sequences that are derived from different polypeptides. A chimeric polypeptide may comprise either modified or naturally-occurring polypeptide. Similarly, "chimeric" in the context of a polynucleotide encoding a chimeric polypeptide includes nucleotide sequences derived from different coding regions.

The term "chimeric polypeptide" refers to a polypeptide which is made by the combination (i.e., "fusion") of two otherwise separated segments of amino sequence, usually through human intervention. A polypeptide that comprises a chimeric amino acid sequence is a chimeric polypeptide. Some chimeric polypeptides can be referred to as "fusion variants."

A "vector" or "expression vector" is a replicon, such as plasmid, phage, virus, or cosmid, to which another nucleic acid segment, i.e., an "insert", may be attached so as to bring about the replication of the attached segment in a cell.

An "expression cassette" comprises a nucleic acid coding sequence operably linked, as defined herein, to a promoter sequence, as defined herein.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

"Operably linked" or "operatively linked" or "operatively associated with," as used interchangeably, refers to a juxtaposition wherein the components so described are in a relationship permitting them to function in their intended manner. For instance, a promoter is operably linked to a coding sequence if the promoter affects its transcription or expression. A nucleic acid molecule is operatively linked or operably linked to, or operably associated with, an expression control sequence when the expression control sequence controls and regulates the transcription and translation of nucleic acid sequence. The term "operatively linked" includes having an appropriate start signal (e.g., ATG) in front of the nucleic acid sequence to be expressed and maintaining the correct reading frame to permit expression of the nucleic acid sequence under the control of the expression control sequence and production of the desired product encoded by the nucleic acid sequence. If a gene that one desires to insert into a recombinant DNA molecule does not contain an appropriate start signal, such a start signal can be inserted in front of the gene.

In accordance with the present invention there may be employed conventional molecular biology, microbiology, and recombinant DNA techniques within the skill of the art. Such techniques are explained fully in the literature. See, e.g., Sambrook et al, 2001, "Molecular Cloning: A Laboratory Manual"; Ausubel, ed., 1994, "Current Protocols in Molecular Biology" Volumes I-III; Celis, ed., 1994, "Cell Biology: A Laboratory Handbook" Volumes I-III; Coligan, ed., 1994, "Current Protocols in Immunology" Volumes I-III; Gait ed., 1984, "Oligonucleotide Synthesis"; Hames & Higgins eds., 1985, "Nucleic Acid Hybridization"; Hames & Higgins, eds., 1984, "Transcription And Translation"; Freshney, ed., 1986, "Animal Cell Culture"; IRL.

As used herein, the terms "top," "bottom," "upper," "lower," "above," and "below" are used to provide a relative relationship between structures. The use of these terms does not indicate or require that a particular structure must be located at a particular location in the apparatus.

Other features and advantages of the invention will be apparent from the following description and the claims.

BRIEF DESCRIPTION OF THE DRAWINGS

FIG. 2 shows a photograph of an exemplary surface acoustic wave device.

FIG. 3A-3B shows the linearized vector sequence for pble-vcp synthetic DNA construct (SEQ ID NO:1).

FIG. 7A shows a schematic showing an exemplary method for sonoporation in a fluidic region 14 in a cartridge interfaced with an acoustic transducer 11 via an optional thermal exchange layer 17, such as in a non-limiting bulk acoustic wave (BAW) transducer. FIG. 7B shows a schematic of a non-limiting surface acoustic wave (SAW) transducer.

DETAILED DESCRIPTION OF THE INVENTION

The present invention relates, in part, to the use of acoustic waves to deliver an agent (e.g., a nucleic acid) to a cell (e.g., a microorganism). In particular, acoustic-based delivery (i.e., sonoporation) of such an agent can be tuned, thereby identifying the optimal frequency to achieve disruption of the cell membrane to facilitate delivery of an agent (e.g., to facilitate transfection) while maintaining viability of the cell. In some embodiments, the present invention employs surface acoustic wave (SAW) and bulk acoustic wave (BAW) transducers to direct localized acoustic pressure in proximity to the cell (e.g., a microorganism, including eukaryotes (e.g., algae), Gram-positive bacteria, and Gram-negative bacteria). When such acoustic waves are provided in the presence of a nucleic acid, then transfection can be promoted.

Figure 7A:
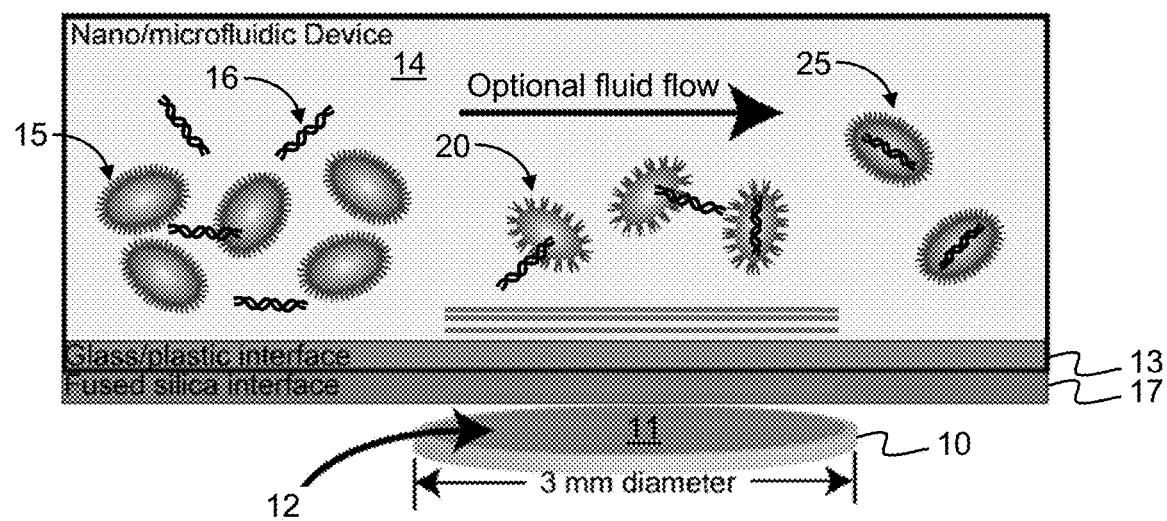
FIG. 7A-7B provides schematics of exemplary systems for employing acoustic-based sonoporation.

FIG. 7A shows the principle of operation of a non-limiting miniature acoustic cell system to provide localized acoustic pressure in proximity to the cell. When an alternating voltage is applied across a piezoelectric transducer 10, the piezoelectric material is strained out-of-the plane, thereby defining the propagation direction. Optionally, the transducer 10 includes a top electrode 11 on the top surface and a bottom electrode (not shown) on the bottom surface. Electrodes can be placed in any useful configuration. In some instances, the device in FIG. 7A uses parallel set electrodes, where each face of the transducer is metallized.

These longitudinal or compression waves 12 travel with a displacement parallel to the propagation direction and through a thermal exchange layer 17 (if present) and an interface 13 into adjoining media, here the fluid region 14 of the device. The thermal exchange layer 17 can include a material having high thermal conductivity and/or high thermal diffusivity, thereby facilitating heat transfer away from the sample.

The interface 13 can include glass, ceramic, thin plastic, or other low-loss acoustic materials, such as silicon. Therefore, the acoustic waves 12 easily penetrate into the fluid-filled region 14 of the cartridge. The acoustic waves 12 have sufficient energy to overcome the intermolecular bonding forces among biological cell enclosures, such as phospholipids, lipid proteins, and peptidoglycans of external and internal membranes for biological cells, including the cellular lipid bilayer membrane, the outer plasma membrane, and internal organelle membranes. Therefore, cells 15 entering the active portion of the fluid region 14 have their cellular membranes disrupted 20 in the presence of an agent (e.g., a nucleic acid 16), thereby providing a transformed cell 25 including the agent. Further details for acoustic cell systems are described herein.

Figure 7B:
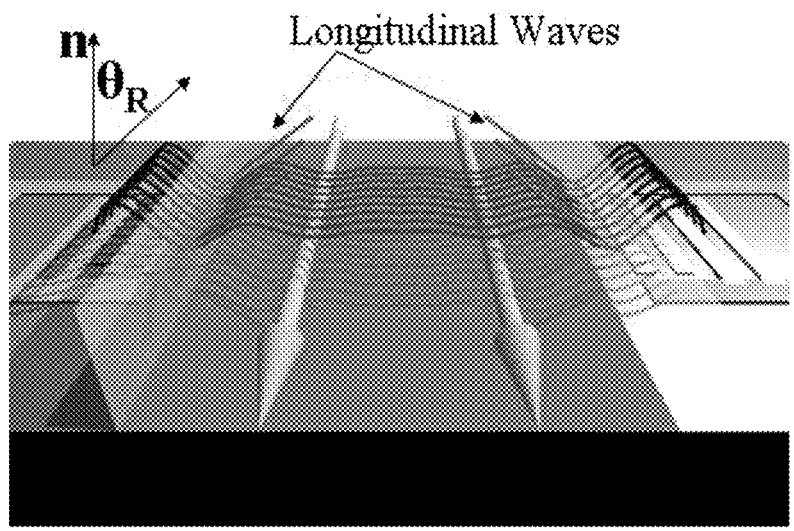

FIG. 7B shows a schematic for a system configured to deliver surface acoustic waves (SAW) to the channel. The type of transducing substrate (e.g., 128° YX lithium niobite) and position of electrodes (e.g., interdigitated electrodes) can be selected to provide longitudinal waves through the channel that are perpendicular to the direction of flow.

In particular embodiments, acoustic-based delivery can be achieved even in the presence of high salt levels. In some embodiments, delivery is conducted under high salinity conditions (e.g., salinity levels of from about 0.05% to about 30%, including from 0.05% to 0.5%, 0.05% to 1%, 0.05% to 2%, 0.05% to 3%, 0.05% to 3.5%, 0.05% to 4%, 0.05% to 4.5%, 0.05% to 5%, 0.05% to 10%, 0.05% to 15%, 0.05% to 20%, 0.05% to 25%, 0.1% to 0.5%, 0.1% to 1%, 0.1% to 2%, 0.1% to 3%, 0.1% to 3.5%, 0.1% to 4%, 0.1% to 4.5%, 0.1% to 5%, 0.1% to 10%, 0.1% to 15%, 0.1% to 20%, 0.1% to 25%, 0.1% to 30%, 0.3% to 1%, 0.3% to 2%, 0.3% to 3%, 0.3% to 3.5%, 0.3% to 4%, 0.3% to 4.5%, 0.3% to 5%, 0.3% to 10%, 0.3% to 15%, 0.3% to 20%, 0.3% to 25%, 0.3% to 30%, 0.5% to 1%, 0.5% to 2%, 0.5% to 3%, 0.5% to 3.5%, 0.5% to 4%, 0.5% to 4.5%, 0.5% to 5%, 0.5% to 10%, 0.5% to 15%, 0.5% to 20%, 0.5% to 25%, 0.5% to 30%, 0.8% to 1%, 0.8% to 2%, 0.8% to 3%, 0.8% to 3.5%, 0.8% to 4%, 0.8% to 4.5%, 0.8% to 5%, 0.8% to 10%, 0.8% to 15%, 0.8% to 20%, 0.8% to 25%, 0.8% to 30%, 1% to 2%, 1% to 3%, 1% to 3.5%, 1% to 4%, 1% to 4.5%, 1% to 5%, 1% to 10%, 1% to 15%, 1% to 20%, 1% to 25%, 1% to 30%, 1.5% to 2%, 1.5% to 3%, 1.5% to 3.5%, 1.5% to 4%, 1.5% to 4.5%, 1.5% to 5%, 1.5% to 10%, 1.5% to 15%, 1.5% to 20%, 1.5% to 25%, 1.5% to 30%, 2% to 3%, 2% to 3.5%, 2% to 4%, 2% to 4.5%, 2% to 5%, 2% to 10%, 2% to 15%, 2% to 20%, 2% to 25%, 2% to 30%, 2.5% to 3%, 2.5% to 3.5%, 2.5% to 4%, 2.5% to 4.5%, 2.5% to 5%, 2.5% to 10%, 2.5% to 15%, 2.5% to 20%, 2.5% to 25%, 2.5% to 30%, 3% to 3.5%, 3% to 4%, 3% to 4.5%, 3% to 5%, 3% to 10%, 3% to 15%, 3% to 20%, 3% to 25%, 3% to 30%, 3.5% to 4%, 3.5% to 4.5%, 3.5% to 5%, 3.5% to 10%, 3.5% to 15%, 3.5% to 20%, 3.5% to 25%, 3.5% to 30%, 4% to 4.5%, 4% to 5%, 4% to 10%, 4% to 15%, 4% to 20%, 4% to 25%, 4% to 30%, 4.5% to 5%, 4.5% to 10%, 4.5% to 15%, 4.5% to 20%, 4.5% to 25%, 4.5% to 30%, 5% to 10%, 5% to 15%, 5% to 20%, 5% to 25%, 5% to 30%, 10% to 15%, 10% to 20%, 10% to 25%, 10% to 30%, 20% to 25%, and 20% to 30%).

Salinity can be determined in any useful manner, such as the measurement of g of salt per kg of solvent (e.g., water). For instance, 30 g of salt per 1 kg of water would provide a salinity level of about 3% or an equivalent level of about 30 parts per thousand (ppt). Exemplary salts include any useful salts, including one or more dissolved salts, including cations and anions, such as sodium ($Na^+$), potassium ($K^+$), magnesium ($Mg^{2+}$), calcium ($Ca^{2+}$), chloride ($Cl^-$), sulfate ($SO_4^{2-}$), etc.

Cells, Including Microorganisms

The present invention can be employed to manipulate any useful host or sample, including algal samples and plant samples, thereby providing a transformed cell that includes an agent (e.g., a nucleic acid). The algae can include any useful organism, such as chlorophyta, diatoms, plankton, protists, and/or cyanobacteria. For instance, algae can include one or more photosynthetic organisms, including one or more microalgae, macroalgae, diatoms, green algae, yellow algae, phytoplankton, plankton, haptophytes, and/or cyanobacteria. Exemplary algae include *Achnanthes, Ankistrodesmus* (e.g., *A. falcatus* or *A. fusiformis*), *Aphanizomenon, Arthrospira* (e.g., *A. maxima*), Bacillariophyceae, *Botryococcus* (e.g., *B. braunii*), *Chlamydocapsa* (e.g., *C. bacillus*), *Chlamydomonas* (e.g., *C. perigranulata* or *C. reinhardtii*), *Chlorella* (e.g., *C. marina, C. vulgaris, C. variabilis, C. sorokiniana, C. minutissima,* or *C. pyrenoidosa*), *chlorococcum* (e.g., *C. infusionum, C. littorale,* or *C. humicola*), *Chlorogloeopsis* (e.g., *C. fritschii*), *Chlorophyceae, Chrysophyceae, Cyanophyceae, Dunaliella* (e.g., *D. bardawil, D. bioculata, D. primolecta, D. tertiolecta,* or *D. salina*), *Ellipsoidion, Haematococcus* (e.g., *H. pluvialis*), *Isochrysis, Kirchneriella* (e.g., *K. lunaris*), *Nannochloropsis* (e.g., *N. salina, N. gaditana,* or *N. oculata*), *Neochloris* (e.g., *N. oleoabundans*), *Nitzschia, Ostreococcus* (e.g., *O. tauri, O. lucimarinus, O. mediterraneus,* and *O.* spp. RCC809), *Phaeodactylum* (e.g., *P. tricornutum*), *Porphyridium* (e.g., *P. purpureum*), *Pyrmnesium* (e.g., *P. parvum*), *Scenedesmus* (e.g., *S. obliquus, S. quadricauda,* or *S. dimorphus*), *Schizochytrium, Skeletonema* (e.g., *S. costatum*), *Spirogyra, Spirulina* (e.g., *S. maxima* or *S. platensis*), *Synechococcus* (e.g., *S. elongatus*), *Tetraselmis* (e.g., *T. maculata* or *T. suecica*), and/or *Thalassiosira* (e.g., *T. pseudonana*). Additional algae species and organisms are described in Schneider R C S et al., "Potential production of biofuel from microalgae biomass produced in wastewater," in *Biodiesel Feedstocks, Production and Applications*, Prof Zhen Fang (ed.), InTech, 2012, 22 pp.; and U.S. Pat. No. 8,119,859, each of which is incorporated herein by reference in its entirety.

Algae can be grown in any useful manner. For instance, the algae can be provided as a monoculture or as a polyculture (e.g., a polyculture turf biomass or benthic algal polyculture turf) grown in a pond, a bioreactor, a field plate, a tank reactor, etc. In addition, the algae can be derived from or grown within any source, including wastewater (e.g., agribusiness, municipal, and/or industrial wastewater), as well as water bodies with excess nutrients. Biomass from high productivity polyculture sources, such as those used for waste water treatment, commonly contain 20-50% protein, 20-40% carbohydrates, 5-20% lipids, and up to 50% ash.

A plant refers to whole plants (e.g., immature or mature whole plants), plant organs (e.g., leaves, stems, buds, flowers, roots, root tips, anthers, seed, grain, embryo, pollen, ovules, cotyledons, hypocotyls, pods, shoots, stalks, etc.), and plant cells (including tissues, tissue cultures, cell, etc.), and progeny of same. Exemplary plants include those amenable to transformation techniques, including both monocotyledonous and dicotyledonous plants, as well as certain lower plants such as algae. Suitable plants include plants of a variety of ploidy levels, including polyploid, diploid, and haploid. Non-limiting plants include tobacco, maize, pea, canola, Indian mustard, millet, sunflower, hemp, switchgrass, duckweed, sugarcane, sorghum, and sugar beet.

Using any agent described herein, the plant can be transformed into a transgenic plant, i.e., a plant that comprises within its cells an exogenous polynucleotide. The term "transgenic" as used herein does not encompass the alteration of the genome (chromosomal or extra-chromosomal) by conventional plant breeding methods (e.g., crosses) or by naturally occurring events such as random cross-fertilization, non-recombinant viral infection, non-recombinant bacterial transformation, non-recombinant transposition, or spontaneous mutation.

Agents

The present invention includes the use of sonoporation to deliver one or more agents to the cell. In particular embodiments, the agent includes a nucleic acid and/or a polypeptide. The nucleic acid can be provided in any useful form, such as RNA, DNA, DNA/RNA hybrids, phage, plasmid, linear forms thereof, concatenated forms thereof, circularized forms thereof, modified forms thereof, single stranded forms thereof, and double stranded forms thereof.

The agent can optionally include a plasmid to encode, express, or modulate any useful target protein, target peptide, and/or target nucleic acid (e.g., any described herein). Exemplary targets include, e.g., a lipase (e.g., a triacylglycerol (TAG) lipase, including TAG lipase CrLIP1 or TAG lipase SDP1), a laminarinase, an oxidase (e.g., alternative oxidase 1, alternative oxidase 2, cytochrome c oxidase, etc.), a dehydrogenase (e.g., isocitrate dehydrogenase, pyruvate dehydrogenase, glycolate dehydrogenase, α-ketoglutarate dehydrogenase, etc.), a ligase (e.g., glycolate carboxyligase), a carboxylase (e.g., pyruvate carboxylase, phosphoenolpyruvate carboxylase, etc.), a reductase (e.g., nitrate reductase, tartronic semialdehyde reductase, etc.), a globular protein (e.g., tubulin including β-tubulin, ferritin, etc.), a metal-binding protein (e.g., metallothionein, a metalloprotein, a metalloenzyme, etc.), a nuclear localization sequence, a light harvesting complex protein (including subunits thereof and complexes thereof, e.g., a chlorophyll binding protein, violaxanthin-chlorophyll a binding protein, etc.), a transferase (e.g., UTP:G1P uridylyltransferase 1, UTP:G1P uridylyltransferase 2, etc.), a coenzyme (e.g., coenzyme A), or a fragment thereof, as well as sequence encoding any of these or a complementary sequence thereof.

In addition, the plasmid can express any useful polypeptide and/or nucleic acid sequence, including a nuclear localization sequence, a cell penetrating peptide, a targeting peptide, a polypeptide toxin, a small hairpin RNA (shRNA), a small interfering RNA (siRNA), a reporter (e.g., a reporter protein), etc. Additional reporters include polypeptide reporters which may be expressed by plasmids (such as histone-packaged supercoiled DNA plasmids) and include polypeptide reporters such as fluorescent green protein and fluorescent red protein. The plasmid can be of any useful form (e.g., supercoiled and/or packaged plasmid). For instance, the plasmid can be a histone-packaged supercoiled plasmid including a mixture of histone proteins.

Further exemplary, non-limiting agents include polynucleotide, such as double stranded linear DNA, minicircle DNA, naked DNA or plasmid DNA (especially ds plasmid DNA, RNA, as well as chimeras, fusions, or modified forms thereof), messenger RNA, small interfering RNA, small hairpin RNA, microRNA, a polypeptide (e.g., a recruitment domain or fragments thereof), a protein (e.g., an enzyme, an initiation factor, or fragments thereof), a drug (in particular, an anticancer drug such as a chemotherapeutic agent), an imaging agent, a detection agent (e.g., a dye, such as an electroactive detection agent, a fluorescent dye, a luminescent dye, a chemiluminescent dye, a colorimetric dye, a radioactive agent, etc.), a label (e.g., a fluorescent label, a colorimetric label, a quantum dot, a nanoparticle, a microparticle, an electroactive label, an electrocatalytic label, a barcode, a radio label (e.g., an RF label or barcode), avidin, biotin, a tag, a dye, a marker, an enzyme or protein that can optionally include one or more linking agents and/or one or more dyes), or a mixture thereof.

Acoustic Cell Systems

Any useful acoustic cell system can be employed to deliver acoustic waves to the cells and/or agent(s). In one embodiment, the system includes a cartridge and a transducer (e.g., a single acoustic transducer or an array including a plurality of acoustic transducers). Such transducers can include SAW or BAW transducers.

To facilitate fluid transport, the cartridge can have one or more channels (e.g., nanofluidic and/or microfluidic channels). The channel can have any useful dimension, such as length, width, height, or cross-section (e.g., rectangular, circular, ellipsoid, triangular, etc.). In addition, any of these dimensions can be uniform (e.g., straight, curved, serpentine, etc.) or variable (e.g., tapered, widened, branched, etc.) along its length. In particular, the cartridge includes an array of channels in any useful format (e.g., a format including a parallel array of channels having a main channel branching into a plurality of channels or an array having a plurality of channels converging into a main channel).

Figure 8:
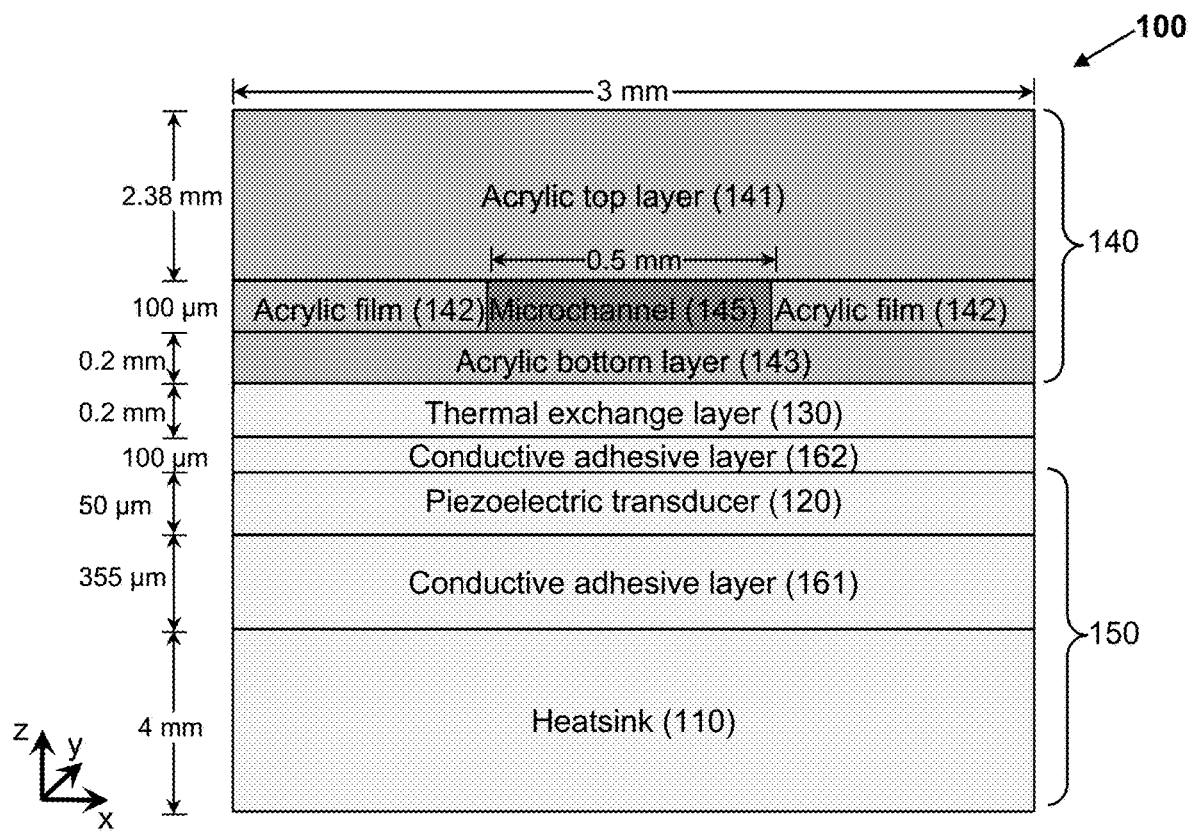
FIG. 8 is a cross-sectional schematic of a portion of an exemplary acoustic cell system 100 having a microchannel 145, a thermal exchange layer 130, and an acoustic transducer 120.

Exemplary cartridges are provided in FIG. 8 and FIG. 9A-9E. FIG. 8 shows a cross-sectional end-view illustration of an exemplary system 100 having a cartridge 140 and a platform 150 having a transducer 120 (e.g., a BAW transducer, such as a 36° Y lithium niobate layer having a thickness of about 50 μm and a diameter of about 3 mm). The cartridge structure was modeled using a 1D transmission line model and finite element modeling, as described in U.S. patent application Ser. No. 12/872,919, filed Aug. 31, 2010, which is incorporated herein by reference in its entirety. In this non-limiting example, the cartridge 140 includes a 0.5 mm wide×100 μm high channel 145 formed in a 100 μm thick acrylic film 142 sandwiched between a 0.2 mm thick acrylic bottom layer 143 and a 2.38 mm thick acrylic top layer 141. Alternatively, the cartridge can be formed within a single layer with a channel formed thereof or multiple layers (e.g., two or more layers) having a channel formed within and/or between the layers. Furthermore, the cartridge can be formed from acrylic or any other useful material (e.g., any polymer or plastic described herein).

A thermal exchange layer can be disposed between the cartridge and the platform. As shown in FIG. 8, the thermal exchange layer 130 can be affixed to the cartridge 140 or to the platform 150. In one embodiment, if the cartridge is to be disposed after a single use, then the thermal exchange layer can be conserved by affixing this layer to the platform. Alternatively, the thermal exchange layer can be a detached layer that is disposed between the cartridge and the platform. In this embodiment, the thermal exchange layer can be mechanically coupled between the cartridge and platform by pressure applied by the platen (e.g., as described herein).

For the exemplary system in FIG. 8, the topside of a 0.2 mm thick aluminum nitride (AlN) thermal exchange layer 130 is mechanically and reversibly coupled to the cartridge structure 140. A one-micron gold top electrode pattern can be defined on the backside surface of the AlN layer 130. A transducer layer 120 (e.g., a 36° Y lithium niobate layer having a thickness of about 50 μm and a diameter of about 3 mm) can be bonded to the gold-patterned backside of the AlN layer 130 using a thin conductive adhesive layer 162 (e.g., 100 μm of conductive epoxy). A voltage can be applied between the top and bottom electrodes to energize the piezoelectric transducer. The transducer is capable of several power settings ranging from gentle mixing to cell membrane disruption. The transducer layer 120 and the AlN layer 130 can then be encapsulated, leaving an opening on the backside of the piezoelectric transducer.

The backside opening can then be backfilled with a thicker conductive adhesive layer 161 (e.g., 355 μm of conductive epoxy), which electrically connects the transducer 120 to an electrical node and thermally to a heat sink 110 (e.g., an aluminum heatsink layer having a thickness of about 4 mm). Exemplary conductive adhesives for the conductive adhesive layers 161, 162 include a conductive material (e.g., silver, gold, copper, or graphite) in a base (e.g., a resin, an epoxy, an acrylate, a cellulose, a solvent, an elastomer, a polyester, or a polymer), such as those available as Epo-tek® E4110 (an electrically conductive, silver-filled epoxy paste) from Epoxy Technology, Inc., Billerica, MA. In addition, one or more conductive adhesive layers can be used to pattern, adhere, or encapsulate the transducer(s), support layer(s), thermal exchange layer(s), and/or heatsink layer(s).

In particular, the heatsink and/or thermal exchange layer facilitates removing heat from the target. For instance, the heat sink can remove heat from the active region and the acoustic transducers. In another instance, the heat sink and the thermal exchange layer dramatically reduces sample heating, which can be critical to preserving the conformation of nucleic acids.

The thermal exchange material can be formed from any useful material. Exemplary materials include aluminum nitride, silicon carbide, silicon nitride, boron nitride, beryllium oxide, copper, silver, gold, graphene, diamond, a thermal epoxy (e.g., a conductive epoxy including an epoxy resin (e.g., a bisphenol A epoxy resin), a curing agent or hardener, and one or more particles of a conductive material, such as silver, nickel, graphite, steel, etc.), stainless steel, or composites thereof. Other materials include any having high thermal conductivity (e.g., a thermal conductivity of about 150 W/m K or greater) and/or high thermal diffusivity (e.g., a thermal diffusivity of $3.14 \times 10^{-6}$ m$^2$/s or greater) to reduce internal heat accumulation. The thermal exchange material can be further processed, such as by dicing, firing, annealing, hot pressing, etc.

Figure 9A:
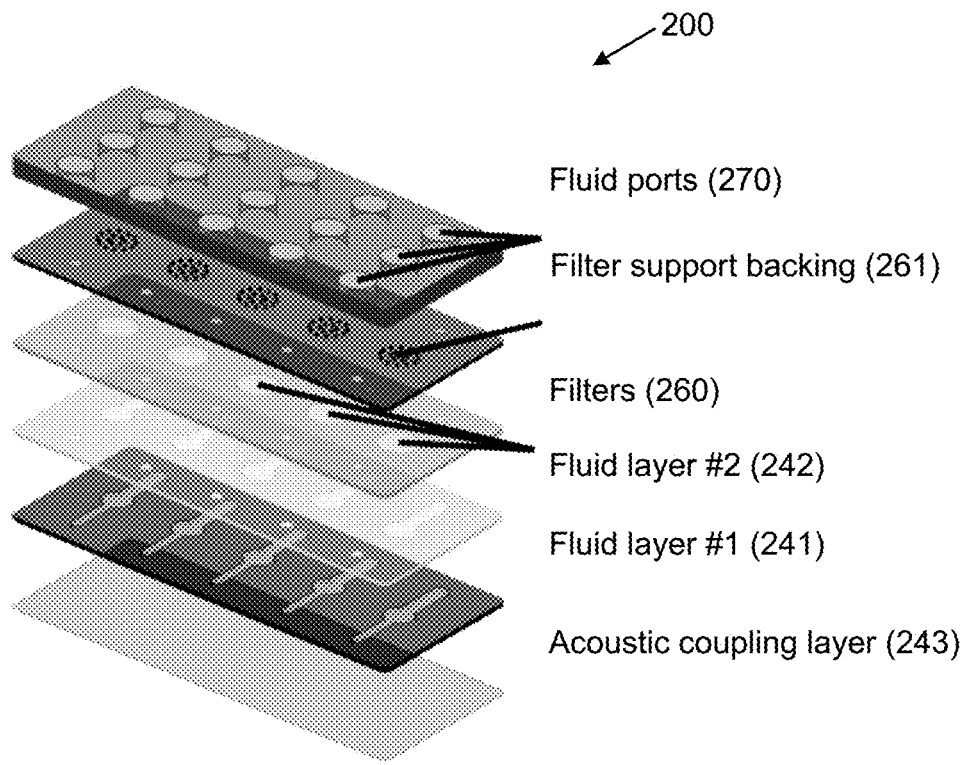
FIG. 9A-9E shows an exemplary acoustic cell cartridge 200. Provided are different perspective of the cartridge: (A) an exploded view showing multiple layers, (B) a plan view showing five microchannel elements 205, (C) a close-up view of element 205 having microchannel 245, and (D) a cross-sectional view of the element 205 along line marked D in FIG. 9B. Also shown is (E) a schematic of the cartridge 200 in use with a cell sample.

As shown in FIG. 9A, an exemplary cartridge structure 200 can include multiple layers. These layers include a plastic acoustic coupling layer 243, two microchannel fluid layers 241, 242, a filter layer 260, a filter support backing layer 261, and a top layer 270 including the fluidic ports and O-ring seals. For example, the cartridge can be a laminated acrylic cartridge. Microchannel features can be cut in a thin cast acrylic sheet (e.g., 100 μm) using a CO$_2$ laser. The acrylic layers can be bonded together using acrylic-based solvents under pressure to create water tight seals between the layers.

Figure 9B:
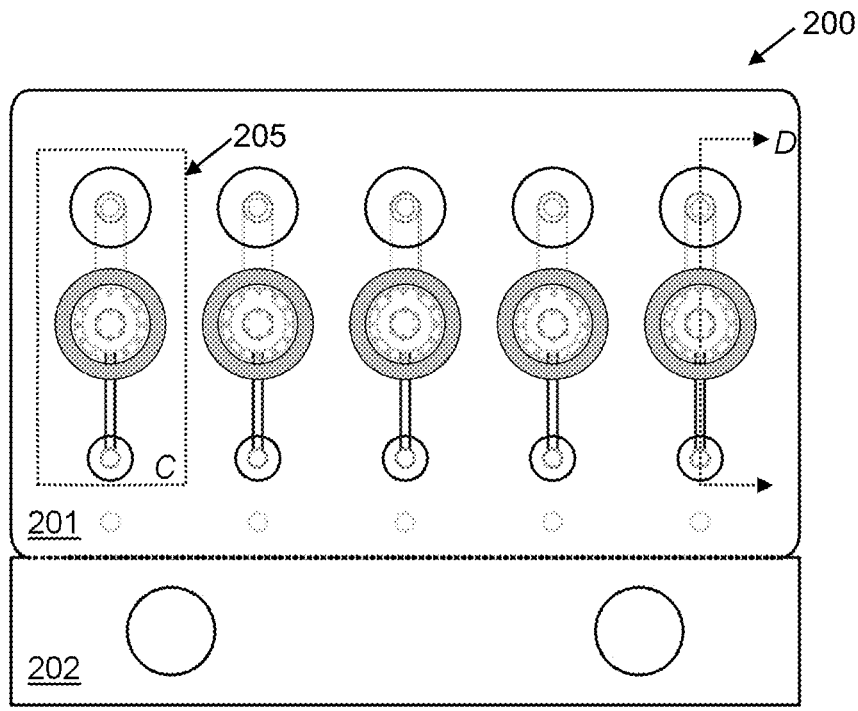
Figure 9C:
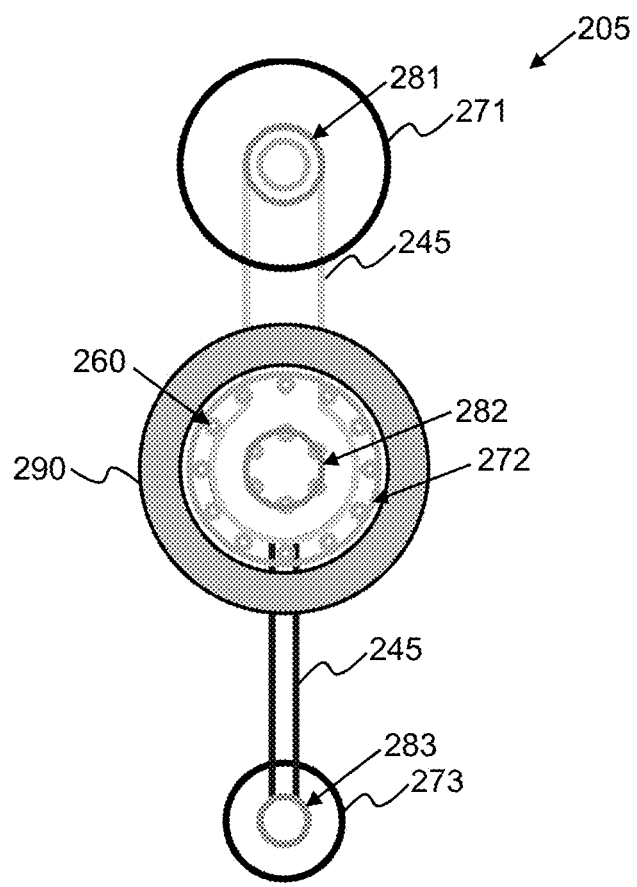

FIG. 9B shows a top-view illustration of a 5-channel disposable cartridge 200 that can be used for parallel sonoporation applications. The multiple channels can be combined together or used separately to build more complex biological processing operations, such as fluid mixing. This cartridge 200 has five independent elements 205 per die 201. In each element, raw sample can be introduced into a fluidic port and flowed over a single bulk acoustic wave transducer and the transformed cells exits the active channel. The bottom section 202 serves as a break-away portion for layer alignment. FIG. 9C shows a magnified view of an element 205, which includes an active channel 245, an inlet 281 to the channel 245, a sample port 271 in fluidic communication with the inlet 281, an outlet 283 to the channel 245, and an exit port 273 in fluidic communication with the outlet 283. The sample and exit ports 271, 273 can optionally include a valve or a gasket.

The cartridge 200 can further include an optional filter 260 for capturing and concentrating the biological cells or targets prior to sonoporation. The element 205 can include a filter 260 in fluidic communication with the active channel 245. One or more inlets/outlets 282 can be included to either withdraw filtered material (e.g., a filtrate, a waste product, etc.) from the channel 245 or to inject one or more reagents through the filter 260. The cartridge can include a port 272 and an o-ring gasket 290 in fluidic communication with the inlet/outlet 282. For instance, stripping buffers and rinse buffers can be removed or introduced through a waste port 282 during collection and release of the cells from the filter 260.

Any useful design consideration can be assessed to optimize the cartridge of the invention. For example, cartridges fabricated in plastic offer a much simpler path toward a disposable cartridge assembly. In another example (e.g., in FIG. 9D), the bottom layer 244 that separates the fluidic region 245 from the transducer 220 is preferably thin or of a rigid material to minimize acoustic loss. Though glass has lower acoustic loss than plastic, a sufficiently thin plastic layer (i.e., about 25 µm) can perform as well as thicker glass layers.

In yet another example, the height of the channel is preferably comparable to the acoustic attenuation length in the fluid and depends on the excited wavelength for optimal propagation distance. Preferably, the acoustic wavelength in the fluid is comparable to the size of the cells to be transformed (e.g., an acoustic wavelength of from about 10 µm to 30 µm, e.g., from 15 µm to 30 µm, 20 µm to 30 µm, or 25 µm to 30 µm). For example, the height of the channel can preferably be less than ten acoustic wavelengths in the fluid and, more preferably, less than a few acoustic wavelengths (e.g., a channel height of from about 15 µm to 300 µm, e.g., from 15 µm to 50 µm, 15 µm to 100 µm, 15 µm to 150 µm, 15 µm to 200 µm, 15 µm to 250 µm, 50 µm to 100 µm, 50 µm to 150 µm, 50 µm to 200 µm, 50 µm to 250 µm, 50 µm to 300 µm, 100 µm to 150 µm, 100 µm to 200 µm, 100 µm to 250 µm, 100 µm to 300 µm, 150 µm to 200 µm, 150 µm to 250 µm, 150 µm to 300 µm, 200 µm to 250 µm, or 200 µm to 300 µm).

In any embodiment herein, the operating frequency of at least one acoustic transducer is of from about 50 MHz to about 100 MHz (e.g., from about 50 MHz to 80 MHz, 50 MHz to 90 MHz, 60 MHz to 80 MHz, 60 MHz to 90 MHz, 60 MHz to 100 MHz, 65 MHz to 80 MHz, 65 MHz to 90 MHz, 65 MHz to 100 MHz, 70 MHz to 80 MHz, 70 MHz to 90 MHz, or 70 MHz to 100 MHz). In some embodiments herein, at least one acoustic transducer is a low frequency transducer. In other embodiments herein, the operating frequency of at least one acoustic transducer (e.g., a focusing transducer) is of from about 0.5 MHz to about 10 MHz (e.g., from about 0.5 MHz to 2 MHz, 0.5 MHz to 5 MHz, 1 MHz to 2 MHz, 1 MHz to 5 MHz, 1 MHz to 10 MHz, 2 MHz to 5 MHz, 2 MHz to 10 MHz, or 5 MHz to 10 MHz).

An exemplary system can employ a platform having one or more acoustic transducers. In particular embodiments, each acoustic transducer is disposed on a transducer array substrate that is reversibly mechanically coupled to a cartridge. The transducer array substrate can include any useful material (e.g., aluminum nitride or fused silica). For instance, as shown in FIG. 9A-9B, the cartridge 200 can include five elements 205, and the platform can then include five acoustic transducers, where each transducer is located beneath each element 205 (e.g., a circular transducer located beneath the portion of the channel underlying each filter 260).

The platform can include any other useful components. For instance, the platform can also include a radiofrequency (RF) driver board configured to electrically connect to the electrode, thereby driving the transducer. The RF driver board can be electrically connected to an RF circuit within the platform. For example, the RF circuit can include a tunable RF source (e.g., a source ranging from about 60 to 80 MHz); a controller electrically connected to the RF source to tune this source; and a RF power amplifier electrically connected to the RF source (e.g., a 2W fixed amplifier, such as Model No. ZHL-1-2W-S available from Mini-Circuits, Brooklyn, NY). Optionally, the RF circuit includes one or more power splitters electrically connected to the amplifier, where each splitter in turn is electrically connected to a transducer (e.g., by way of a contact pad on the electrode electrically connected to that transducer).

The system can also include a platen, which provides mechanical contact between the cartridge and the platform. This contact can be reversible. In addition, the platen can be configured to provide one or more fluidic connectors (e.g., valves, tubing, etc.) that interface with the inlets, outlets, and/or ports of the cartridge. With this configuration, the platen provides a streamlined way to inject, transport, and receive fluid into and out of the cartridge. For instance, the platen can provide fluidic communication between an off-chip pumping system (e.g., any described herein) and the cartridge or between two separate cartridges.

The platform includes one or more acoustic transducers to provide a compression wave for sonoporation. Generally, the transducer includes a piezoelectric material or piezoelectric crystal. Such materials and crystals are characterized by a linear coupling between electrical and mechanical states. Thus, an applied electrical charge induces internal mechanical strain in the material, and, conversely, an applied mechanical strain generates internal electrical charge. These mechanical forces are delivered to the sample in the form of acoustic waves.

The characteristics of the acoustic wave depend on the type and crystal orientation of the transducer material. Exemplary materials include lithium niobate ($LiNbO_3$, e.g., 36° Y-cut $LiNbO_3$ or 128° YX $LiNbO_3$), potassium niobate ($KNbO_3$), lithium tantalate ($LiTaO_3$, e.g., 36° YX-cut $LiTaO_3$), quartz ($SiO_2$), lanthanum gallium silicate, lead zirconate titanate (Pb(Zr, Ti)$O_3$ or PZT, e.g., PZT-5H), polycrystalline lead titanate (PbTiO$_3$), PZN-PT, ceramics (e.g., Pb(Mg$_{1/3}$Nb$_{2/3}$)$O_3$—PbTiO$_3$ (PMN-PT), barium titanate (BaTiO$_3$), lead zirconate-lead titanate ([PbZr$_x$Ti$_{1-x}$O$_3$]-

PZT), and lead titanate (PbTiO$_3$, PCT)), as well as single crystals, composites, laminates, and stacks thereof. Additional materials are provided in Shung K K et al., "Piezoelectric materials for high frequency medical imaging applications: a review," *J. Electroceram.* 2007; 19:139-45, which is incorporated herein by reference in its entirety.

Each acoustic transducer can have any useful dimension (e.g., length, width, height, thickness t, or cross-section), geometry (e.g., rectangular or triangular patches, disks, cones, cylinders, spheres, annuli, tubes, rods, pillars, etc.), and/or crystal orientation (e.g., an orientation that provides longitudinal or quasi-longitudinal waves, such as a 360 or 10° rotated Y-cut or Z lithium niobate). Furthermore, when transducers are provided in an array, each transducer in the array can be the same or different. For instance, to effect both acoustic focusing and sonoporation, the array can include one or more transducers having thickness $t_1$ for focusing and other transducer(s) having thickness $t_2$ for sonoporation, where $t_1 > t_2$.

Any useful acoustic transducer, as well as arrays thereof, can be included in the platform. For instance, the array can include a plurality of transducers, where each transducer is configured to be disposed beneath an active channel in the cartridge. Alternatively, a portion of the transducers can be dedicated to sonoporation, and another portion for other uses (e.g., mixing, microcentrifuging, injecting, assaying, lysing, pumping, etc.). In some embodiments, the transducer is capable of several power settings ranging from gentle mixing to cell membrane lysis.

To minimize cavitation (i.e., rapid formation and collapse of bubbles in a fluid), each transducer can be configured to deliver less than about 240 mW (e.g., to deliver from about 10 mW to about 240 mW, such as from 10 mW to 200 mW, 10 mW to 150 mW, 10 mW to 100 mW, 10 mW to 60 mW, 10 mW to 50 mW, 10 mW to 40 mW, 10 mW to 20 mW, 20 mW to 240 mW, 20 mW to 200 mW, 20 mW to 150 mW, 20 mW to 100 mW, 20 mW to 60 mW, 20 mW to 50 mW, 20 mW to 40 mW, 40 mW to 240 mW, 40 mW to 200 mW, 40 mW to 150 mW, 40 mW to 100 mW, 40 mW to 60 mW, or 40 mW to 50 mW).

The transducer can have one or more electrodes or contact pads providing electrical energy. For instance, the transducer can include a top electrode and a bottom electrode to energize the piezoelectric transducer. Referring to FIG. 8, the top electrode can be disposed between conductive adhesive layer 162 and transducer 120, and the bottom electrode can be disposed between the transducer 120 and the conductive adhesive layer 161. Optionally, a contact pad can be disposed on the top surface of a transducer substrate to provide electrical connection to the bottom electrode of the transducer (e.g., on transducer substrate). The electrode(s) can be formed from any useful material (e.g., gold, chrome, silver, titanium, aluminum, nickel, palladium, platinum, and combinations thereof) and any useful technique (e.g., vacuum deposition, electroless depositions, etc.).

Figure 9D:
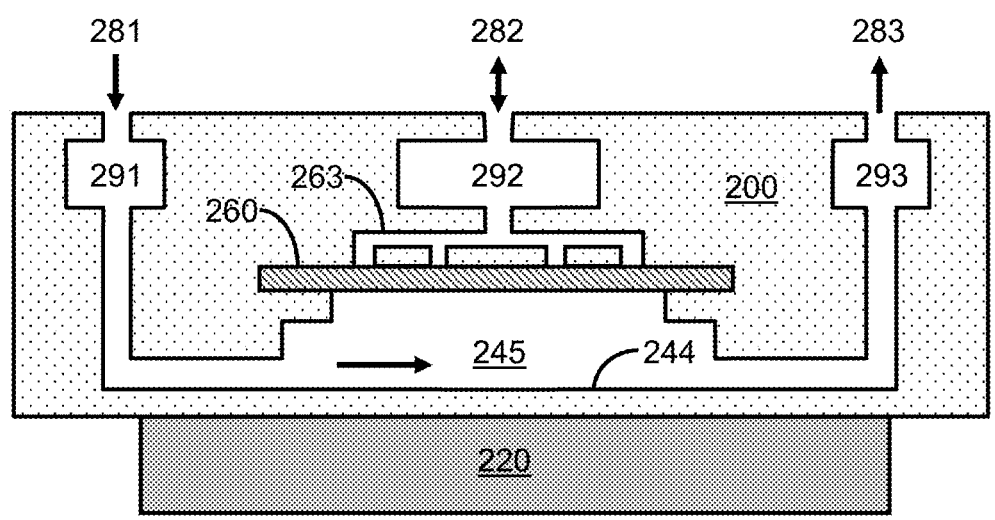

An exemplary acoustic cell system is provided in FIG. 9D. Here, a miniature acoustic cell system is used for sonoporation by localized acoustic pressure. The system includes a high-frequency bulk acoustic wave (BAW) transducer 220 mechanically and reversibly coupled to a disposable microfluidic cartridge 200 having a channel 245 formed therethrough. Although, this system can be adapted to provide a SAW transducer. Reversible mechanical coupling of the cartridge 200 to the BAW transducer 220 enables reuse of the transducer assembly 220 while permitting disposal of the contaminated cartridge 200 after sonoporation. Alternatively, the transducer can be monolithically integrated with the microfluidic channel on the same substrate. As described herein, the system can include a heat sink and/or a thermal exchange layer to minimize sample heating.

Whole cells and agent(s) enter the channel 291 through an inlet 281. The whole cells can then flow through and be disrupted in an active portion of the channel 245 by acoustic pressure generated by the proximate transducer 220. Optionally, the bottom layer 244 that separates the fluidic region 245 from the transducer 220 is preferably thin, composed of a thermal exchange material, and/or includes a rigid material to minimize acoustic loss. Transformed cells (i.e., cells including an agent) can exit the channel 245 through an outlet 283. The cartridge 200 can optionally include a filter 260 and/or a filter support structure 263 including one or more channels. Through inlet/outlet 282 in fluidic communication with filter 260, filtrate can be removed or a reagent can be injected into the channel 245. Connection regions 291, 292, 293 can include one or more seals to connect the inlet/outlet of the cartridge to a pumping system.

Figure 9E:
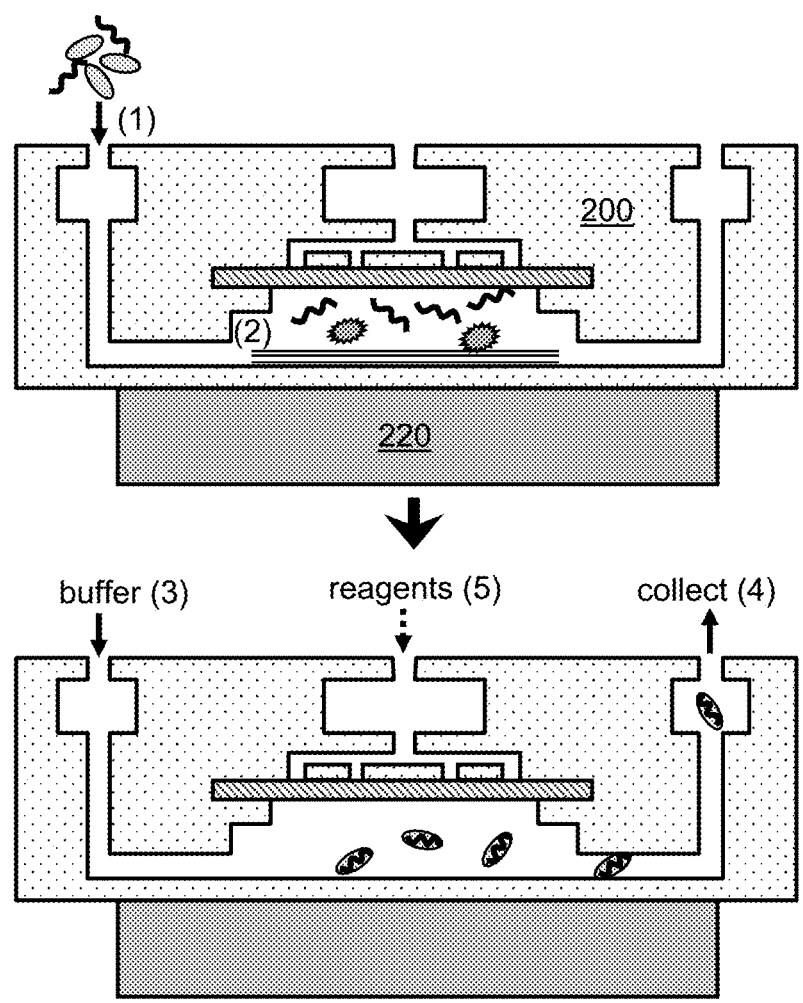

In use (as shown in FIG. 9E), raw samples including cells and agent(s) (1) are introduced into the cartridge 200. Next, an electric field is applied to the transducer 220, thereby producing acoustic waves (2) of sufficient power for sonoporation of the cells in the presence of the agents. Then, a buffer (3) is introduced into the cartridge to transport the transformed cells through the channel by lateral flow. Finally, the transformed cells are collected (4). Optionally, one or more reagents (5) can be provided before, during, or after sonoporation. Furthermore, transformed cells may be optionally incubated on-chip.

Further components of an acoustic cell system can include those described in U.S. Pat. Nos. 7,942,568, 9,512,421, and 9,096,823, each which is incorporated herein by reference in its entirety. Yet other structures and components (e.g., piezoelectric materials, electrodes, acoustic waveguides, acoustic reflectors, etc.) are described in U.S. Pat. No. 8,425,749; Branch D W et al., "Rapid nucleic acid extraction and purification using a miniature ultrasonic technique," *Micromachines* 2017; 8:228; Branch D W et al., "Nucleic acid extraction using a rapid, chemical free, ultrasonic technique for point-of-care diagnostics," *IEEE International Ultrasonics Symposium Proceedings*, held on 3-6 September 2014, pp. 501-6; Branch D W et al., "Intelligent front-end sample preparation tool using acoustic streaming," Sandia Report No. SAND2009-6193, September 2009 (70 pages); Yeo L Y et al., "Ultrafast microfluidics using surface acoustic wave," *Biomicrofluidics* 2009 Jan. 2; 3(1):12002 (23 pages); Yeo L Y et al., "Surface acoustic wave microfluidics," *Annu. Rev. Fluid Mech.* 2014; 46:379-406; Jung B et al., "Acoustic particle filter with adjustable effective pore size for automated sample preparation," *Anal. Chem.* 2008 Nov. 15; 80(22):8447-52; Ai Y et al., "Separation of *Escherichia coli* bacteria from peripheral blood mononuclear cells using standing surface acoustic waves," *Anal. Chem.* 2013 Oct. 1; 85(19):9126-34; Shi J et al., "Continuous particle separation in a microfluidic channel via standing surface acoustic waves (SSAW)," *Lab Chip,* 2009 Dec. 7; 9(23):3354-9; Adams J D et al., "Integrated acoustic and magnetic separation in microfluidic channels," *Appl. Phys. Lett.* 2009 Dec. 21; 95(25):254103 (3 pages); Ravula S K et al., "A microfluidic system combining acoustic and dielectrophoretic particle preconcentration and focusing," *Sens. Actuat. B* 2008; 130:645-52; Adams J D et al., "Tunable acoustophoretic band-pass particle sorter," *Appl. Phys. Lett.* 2010 Aug. 9; 97(6):064103 (3 pages); and Yang A H J et al., "Acoustophoretic sorting of viable mammalian cells in a microflu- Uses The methods herein can be employed to provide an improved plant or alga, which in turn can be further processed to provide any useful product (e.g., a biofuel including biodiesel or bioethanoal, a biomass, a lipid, a co-product, a feed, a fertilizer, a pharmaceutical intermediate, and other useful building blocks).

A plant or algal biomass can be incubated with nutrient-loaded water and sunlight to promote growth, and then harvested. Typically, an algal biomass will include equal fractions of proteins, carbohydrates, and lipids (collectively, biocomponents). Further treatment steps can be employed to breakdown these biocomponents of the plant or algal biomass and release useful residuals.

Lipids from the biomass can be captured by distillation, by lipid disruption, by osmotic stress, by mechanical disruption, and/or by solvent co-extraction. Lipids, including lipid vesicles and microparticles, can be extracted by lipophilic solvents, such as hexane and ethyl acetate, avoiding high energy fractional distillation of the >C2 alcohol and lipid products. Any useful distillation and extraction techniques can be employed, including flash extraction, ionic liquid extraction, etc., to isolate one or more biocrude oil, aqueous phases, aqueous co-products, nutrients, etc.

Phase separation steps can be employed to separate components of a liquefied mixture, fermentation broth, aqueous fraction, a non-aqueous fraction, alcohol fraction, etc. Such steps include any that separate liquid from solid phases, as well as separate two or more phases that can be differentiated based on solubility, miscibility, etc. (e.g., as those present in non-aqueous phases, aqueous phases, lipophilic phases, etc.) in any useful solvent (e.g., an organic solvent, an aqueous solvent, water, buffer, etc.). Phase separation techniques include flash separation (e.g., separation of a fraction into biocrude oil, biocomponents, lipids, solid residuals, aqueous phase, and/or aqueous co-products), acid absorption (e.g., absorption of acid in a matrix to provide recovered nutrients and water for recycled use), filtration, distillation, solvent extraction, ion liquid extraction, etc. The resultant products and co-products can include one or more intermediate products that can optionally be processed to form useful end-use products.

Hydrotreatment is generally used to convert compositions (e.g., including any useful fraction of the plant or algal biomass) into useful intermediate products or end-use products. Such hydrotreatment generally includes use of high temperatures to institute any useful chemical change, e.g., to break apart triglycerides; to form low molecular weight carbon species, such as optionally substituted alkanes, cycloalkanes, or aryls; to saturate carbon chains with hydrogen; to denitrogenate species; and/or to deoxygenate species to form alkanes, such as n-alkanes.

Hydrotreatment can include isomerization, hydrocracking, distillation, hydrodeoxygenation, catalytic processing (e.g., such as use of one or more catalysts to remove nitrogen, oxygen, and/or sulfur from a fraction under any useful condition, such as a pressure of from about 5 MPa to about 15 MPa and a temperature of from about 200° C. to about 450° C.), liquefaction (e.g., such as hydrothermal liquefaction (HTL) or catalytic liquefaction of one or more lipids into a biofuel or a biofuel intermediate by use of an operating temperature of from about 100° C. to about 500° C.), transesterification (e.g., treatment of one or more lipids with an alcohol and an optional catalyst to produce methyl ester biodiesel), and/or catalytic hydrothermal gasification (CHG) (e.g., of an aqueous co-product into biogas).

The hydrotreatment process can employ any useful catalyst (e.g., a metal catalyst, such a copper-based catalyst (e.g., CuCr, CuO), a nickel-based catalyst (e.g., NiMo), a ruthenium-based catalyst, a palladium-based catalyst (e.g., Pd/C), a platinum-based catalyst, a rhenium-based catalyst, or a cobalt-based catalyst (e.g., CoMo)) in the presence of any carrier (e.g., a zeolite, an alumina, etc.); any useful reagent, such as hydrogen (e.g., $H_2$) or water (e.g., supercritical water); any useful pressure, e.g., such as from about 3 MPa to about 30 MPa (e.g., from about 5 MPa to about 20 MPa); and/or any useful temperature, e.g., such as from about 100° C. to about 500° C. (e.g., from about 250° C. to about 350° C.). Further exemplary hydrotreatment conditions are described in Ma F et al., "Biodiesel production: a review," *Bioresource Technol.* 1999; 70:1-15; Tran N H et al., "Catalytic upgrading of biorefinery oil from micro-algae," *Fuels* 2010; 89:265-74; and Wildschut J et al., "Catalyst studies on the hydrotreatment of fast pyrolysis oil," *Appl. Catalysis B* 2010; 99:298-306, each of which is incorporated herein by reference in its entirety.

Exemplary biofuels formed by hydrotreatment include naphtha, biodiesel (e.g., including one or more unsaturated fatty acids or fatty acid esters, such as of from about 10% to about 35% of a long chain fatty acid having a $C_{13}$-$C_{21}$ tail, such as a palmitic fatty acid ($C_{16}$ tail), linoleic fatty acid ($C_{18}$ tail), oleic fatty acid ($C_{18}$ tail), and/or stearic fatty acid ($C_{18}$ tail)), green diesel, renewable aviation fuel, hydrocarbons (e.g., light hydrocarbons), alcohol (e.g., ethanol; propanol, such as 1-propanol; butanol, such as n-butanol, isobutanol, 2-butanol, 3-butanol, 2-methyl-1-butanol, 3-methyl-1-butanol, etc.), and/or a biogas (e.g., hydrogen or methane). Other products formed by hydrotreatment include solid residuals (e.g., biochar and ash), aqueous co-products (e.g., ketoacids, amines, nutrients, etc.), as well as other useful co-products (e.g., animal feed, fertilizer, glycerine, biopolymers, etc.).

EXAMPLES

Example 1: Sonoporation for High-Efficiency Transfection of *Nannochloropsis* Species Eukaryotic algae are excellent candidates for alternative energy due to their high photosynthetic efficiencies and ability to directly convert carbon dioxide ($CO_2$) into triacylglycerides. A primary obstacle in the commercialization of algal biofuels is that the biomass productivities of natural algal strains are not sufficient to support large-scale production of a low-value commodity like fuel. Genetic modification may therefore be employed to meet the biomass productivity goals required for sustainable algal biofuels production. Algal genetic modification has traditionally been limited to model strains, e.g., the freshwater alga *Chlamydomonas reinhardtii*, rather than more robust and salt tolerant strains ideal for biofuels production, such as *Nannochloropsis* species. Here, we describe tools for DNA delivery of constructs to optimize gene expression in two *Nannochloropsis* species: *Nannochloropsis oceanica* CCMP 1779 and *Nannochloropsis* gaditana CCMP 526. Of course, these tools could be applied to different types of cells and microorganisms that would benefit from such delivery methods.

Generally, transfection of *Nannochloropsis* species via electroporation requires numerous wash steps to prevent arcing and suffers from low transfection efficiencies. The low transfection efficiencies via electroporation are likely due to insufficient pore formation in the tough cell wall of *Nannochloropsis* species. As described herein, acoustic based transfection methods (i.e., sonoporation) are not affected by salt concentrations and are highly tunable to optimize cell wall damage. In particular, we investigated two types of sonoporators: surface acoustic wave (SAW) and bulk acoustic wave (BAW) devices (see, e.g., U.S. Pat. Nos. 9,096,823 and 9,512,421, each of which is incorporated herein by reference in its entirety). The following Examples provide results from an exemplary SAW device.

Example 2: Tuning Cell Viability in Electroporation Versus Sonoporation Methods

Using a SAW device, the viability of *N. oceanica* CCMP 1779 was tested with varying power and duration, and standard electroporation conditions were also applied to the same cells for a direct comparison. For other organisms, such as *Saccharomyces cerevisiae*, optimal transfection efficiencies are achieved with approximately a 50% loss of cell viability (see, e.g., Delorme E, "Transformation of *Saccharomyces cerevisiae* by electroporation." *Appl. Environ. Microbiol.* 1989; 55(9):2242-6).

As an example of the application of sonoporation, we demonstrated transfection of algal species: *Nannochloropsis oceanica* CCMP 1779 and *Nannochloropsis* gaditana CCMP 526. First, the power supply to the SAW device was optimized to demonstrate a 20-50% reduction in cell viability for *N. oceanica* CCMP 1779 and *N. gaditana* CCMP 526 (FIG. 1B).

Figure 1A:
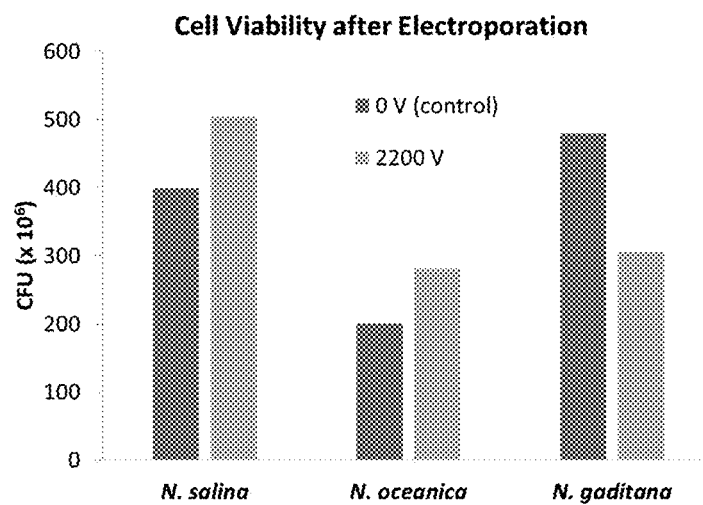
FIG. 1A-1B shows cell viability of *Nannochloropsis* species (A) after electroporation and (B) after sonoporation. Cell viability was measured as CFUs on dilution plates.
Figure 1B:
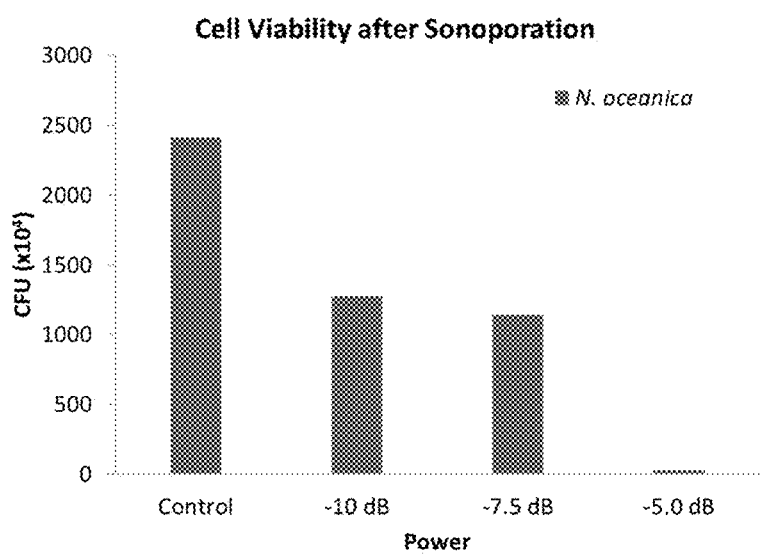

For comparison, high voltage electroporation, a transfection method for *Nannochloropsis* species commonly used but with low transfection efficiencies, was included as a control (see, e.g., FIG. 1A). No significant change in cell viability was observed with electroporation of three *Nannochloropsis* species, which may be responsible for the low transfection efficiencies with this method. Sonoporation, on the other hand, demonstrated tunable control over cell viability by variation of the power supplied to the transducer (see, FIG. 1B).

To demonstrate transfection in *N. oceanica* CCMP 1779 and *N. gaditana* CCMP 526, a SAW device (FIG. 2) was used to transfect a linearized vector containing the ble gene (encoding the bleomycin resistance protein) conferring resistance to zeocin driven by the VCP1 promoter and terminator regions from *N. gaditana* CCMP 526 (FIG. 3A-3B, SEQ ID NO:1). The power supplied to the transducer was varied with an exposure time of 1 minute or 30 seconds.

Example 3: Enhancing Uptake in *Nannochloropsis* Species Using Sonoporation

Some preliminary studies suggest that sonoporation may be a viable method for transfection of algae (see, e.g., Azencott H R et al., "Influence of the cell wall on intracellular delivery to algal cells by electroporation and sonication," *UltrasoundMed. Biol.* 2007; 33(11):1805-17; and Wu X et al., "Ultrasound-mediated intracellular delivery of fluorescent dyes and DNA into microalgal cells," *Algal Res.* 2016; 15:210-6), yet these studies used high frequency acoustic devices with significant heat generation, resulting in cell death. The SAW and BAW devices herein produce lower heat inputs in the liquid culture, providing improved conditions for sonoporation.

Figure 4:
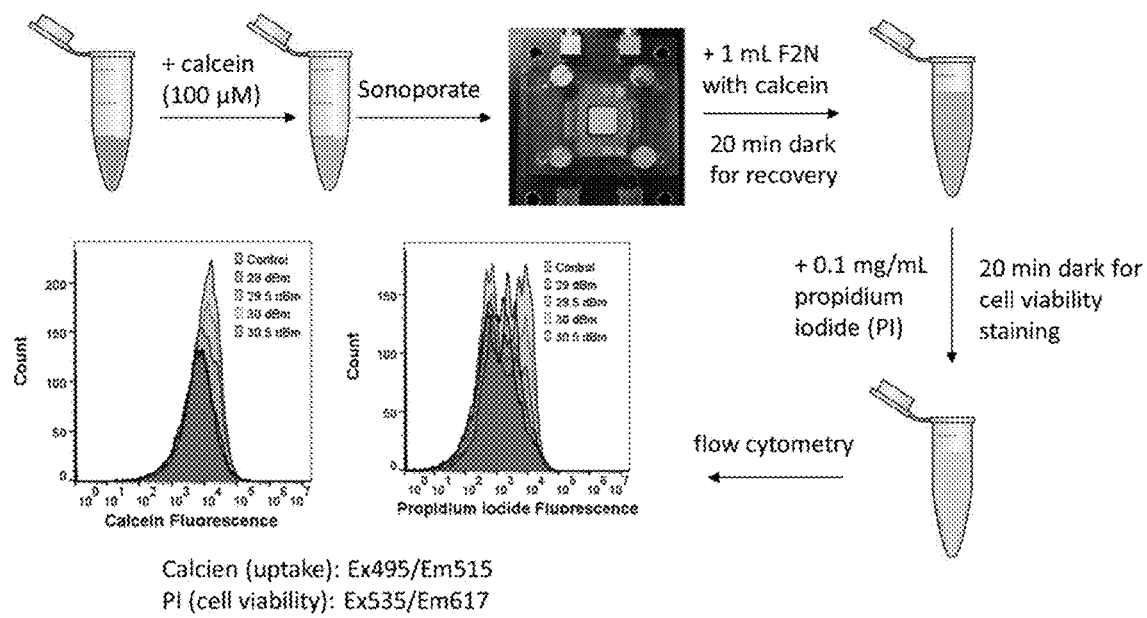
FIG. 4 shows a two-dye protocol for measuring cell membrane permeability in *Nannochloropsis* species. First, a membrane impermeable dye (e.g., calcein) is added prior to sonoporation to quantify uptake. After a recovery period, a second membrane-impermeable dye (e.g., propidium iodide) is added to assess cell viability. Dye fluorescence is measured using flow cytometry.
Figure 5:
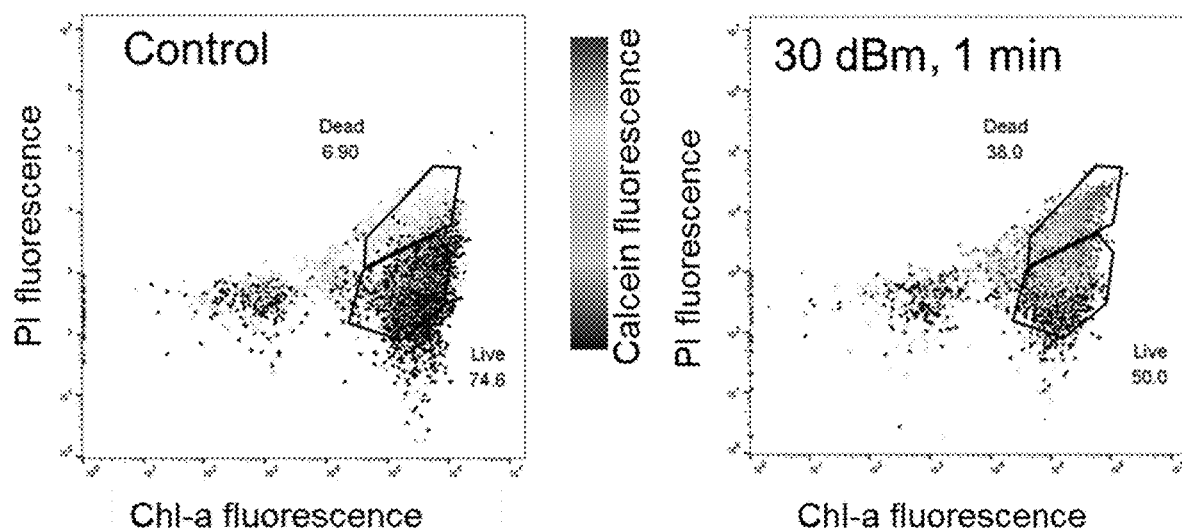
FIG. 5 shows use of the two-dye protocol to determine uptake (high calcein fluorescence) in the live cell population (low PI fluorescence) of *N. oceanica* cells. Data are provided for a control culture (left) and a sonoporated culture (right).
Figure 6:
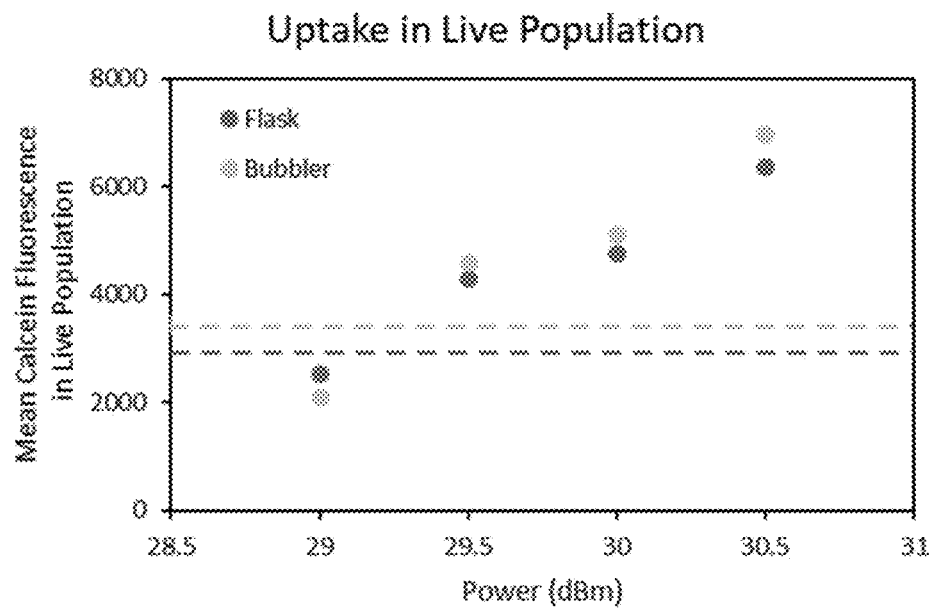
FIG. 6 shows cellular uptake in the live cell population of *N. oceanica* cells, which was quantified across different power settings on the sonoporator and for different growth conditions (shake flask vs. bubbler). Dashed lines indicate values for a control culture (with no sonoporation).

A two-dye protocol was applied to assess uptake efficiency in *Nannochloropsis* species with variable sonoporation conditions (FIG. 4). Using the two-dye protocol, uptake in live *N. oceanica* cells was quantified in the presence and absence of sonoporation (FIG. 5). Further studies revealed the effect of power setting on uptake (FIG. 6), in which a power setting of 29.5-30.5 dBm led to high uptake of dye in *N. oceanica* cells with 1 minute of sonoporation. As can also be seen, uptake efficiencies with sonoporation were independent of culture conditions (shake flask vs. bubbling). Overall, sonoporation methods show potential for improved transfection of microorganisms, including *Nannochloropsis* species, based on viability assessments and uptake measurements.

Example 4: Experimental Methods

The following provide exemplary methods for data provided herein.

Materials: Chemicals described herein were purchased from Fisher Scientific.

Cultivation and cell preparation for *N. oceanica* and *N. gaditana*: *N. oceanica* CCMP 1779 and *N. gaditana* CCMP 526 were grown in either F2N or F2N—NO$_3$ media.

F2N medium included (per liter): 34.12 g Oceanic Natural Sea Salt mix, 10 mL of 1M Tris-HCl buffer (pH 7.5), 0.2675 g NH$_4$Cl, 5 mL of 5 g/L NaH$_2$PO$_4$·H$_2$O solution, 5 mL of trace elements solution, 0.25 mL of thiamine hydrochloride solution, 1 mL of vitamin B12 solution, and 1 mL of biotin solution. Trace elements solution included (per liter): 0.046 g of ZnSO$_4$·7H$_2$O, 0.304 g of MnSO$_4$·H$_2$O, 0.0146 g of Na$_2$MoO$_4$·2H$_2$O, 0.028 g of CoSO$_4$·7H$_2$O, 0.0136 g of CuCl$_2$·2H$_2$O, 9.2 g of Fe(NH$_4$)$_2$·(SO$_4$)$_2$·6H$_2$O, and 8.8 g of Na$_2$EDTA·2H$_2$O. Thiamine hydrochloride solution contained 11 g of thiamine hydrochloride in 1 L of 50 mM HEPES buffer solution (pH 7.8). Vitamin B12 solution contained 0.675 g of vitamin B12 in 1 L of 50 mM HEPES buffer solution (pH 7.8). Biotin solution contained 0.125 g of biotin in 1 L of 50 mM HEPES solution (pH 7.8).

For F2N—NO$_3$ medium, the ammonium chloride was replaced with 2.16 g of NaNO$_3$ (per L), and the phosphate solution was increased 4×. Both F2N and F2N—NO3 media, along with the vitamin solutions were filter sterilized with a 0.22 µm filter. The phosphate and trace elements stock solutions were autoclaved for sterilization.

*N. gaditana* CCMP 526 and *N. oceanica* CCMP 1779 were maintained on 1.5% agar plates of F2N or F2N—NO$_3$ media. Cultures were transferred from agar plates to 4 mL of liquid medium in a 16 mm glass test tube with vented cap. The inoculum was cultivated at room temperature and 150 rpm under 80 µmol photons m$^{-2}$ s$^{-1}$ (about 100 µE) illumination from alternating cool white and plant fluorescent lights. After sufficient growth (approximately 5 to 7 days), the entire 4 mL culture was transferred into 100 mL of media in a 500 mL baffled Erlenmeyer flask and grown under the previously described conditions for about 3 to 5 days.

For shake flask cultivation, 10 mL of this secondary culture were transferred to 500 mL baffled Erlenmeyer flasks containing 140 mL of medium each. For bubbled cultures, the entire 100 mL secondary culture was transferred to 700 mL of fresh medium in a 1 L glass bottle with 3-port cap for bubbling and venting with a 0.22 µm filter. When the culture reached a desired cell density, the cells were prepared for sonoporation and electroporation.

For each transfection reaction, 250 mL of culture was centrifuged at 3,000×g for 10 min. at room temperature. The cell pellet was washed with 50 mL of 375 mM sorbitol solution four times (centrifuged at 3,000×g for 10 min.), followed by five 1 mL washes (centrifuged at 3,000×g for 5 min.). The cell pellet was resuspended in 100 µL of 375 mM sorbitol, and the entire volume is used for a single transfection reaction. Additional details are described below.

Strains and preparation of DNA: Plasmid DNA containing the zeocin resistance cassette (pble-vcp, FIG. 3A-3B, SEQ ID NO:1) was prepared from overnight *Escherichia coli* DH5α/pble-vcp cultures. Alternatively, primers and DNA oligonucleotide gblocks were provided from Integrated DNA Technologies (IDT). Plasmid purification was performed using a QIAprep spin miniprep kit (Qiagen) with 30 µL of ultrapure water to elute the plasmid DNA. Isolated pble-vcp was then linearized using ScaI (New England Biolabs) digestion, and the linearized plasmid was purified using a QIAquick PCR purification kit (Qiagen) with ultrapure water for elution. The purified, linearized plasmid was quantified using a Nanodrop spectrometer, and 1 µg of DNA in 10 µL of ultrapure water was added to each transfection reaction.

Sonoporation using surface acoustic wave and bulk acoustic wave devices: Cultures of *N. oceanica* CCMP 1779 and *N. gaditana* CCMP 526 were grown as previously described in either F2N or F2N—NO$_3$ media. Cells were prepared for sonoporation using two methods: (1) the electroporation preparation method as described herein, yet for sonoporation, the final cell culture was diluted 100× and 1000× with 375 mM sorbitol solution; and (2) the quick preparation method requires either 25 mL of *N. oceanica* CCMP 1779 at OD$_{750}$=0.4 or 50 mL of *N. gaditana* CCMP 526 at OD$_{750}$=0.2. The cultures are centrifuged once at 3,900×g for 10 min at room temperature in a conical centrifuge tube and resuspended in 375 mM sorbitol solution to a final volume of approximately 100 µL.

To optimize sonoporation conditions, a dual dye method, similar to those previously used for algal sonoporation was used (see, e.g., Azencott H R et al., *Ultrasound Med. Biol.* 2007; 33(11):1805-17; and Wu X et al., *Algal Res.* 2016; 15:210-6). A 2 mM solution of calcein dissolved in dimethyl sulfoxide (DMSO) was added to 100 µL of culture to a final concentration of 100 µM.

The mixture was transferred to a custom sonoporation devices, which were constructed at Sandia National Laboratories (see, e.g., U.S. Pat. Nos. 7,942,568, 8,436,509, 9,096,823 and 9,512,421, each of which is incorporated herein by reference in its entirety). Surfaces of the SAW or BAW devices were decontaminated using 70% ethanol. The sonoporation device included a PDMS chamber sealed with an o-ring and screws on top of a surface acoustic wave (SAW) or bulk acoustic wave (BAW) transducer with heat sink, connected to a Mini-Circuits RF power amplifier (model TIA-1000-1R8) and Agilent 8648A 100 kHz-1000 MHz signal generator. The frequency on the signal generator (Agilent 8648A) was tuned so that a change in the surface tension was observable at the start of the acoustic signal yet no surface movement was visible during delivery of the acoustic signal. The signal generator provided an acoustic signal (−10 to −5 dBm) to an amplifier (Mini-Circuits RF Power Amplifier, Model TIA-1000-1R8) with a gain of 35 dBm. The SAW device was operated at a frequency of 96.62040 MHz with varying power (29-30.5 dBm) and duration (30 sec or 1 min).

The sonoporated culture was transferred to a 1 mL solution of F2N or F2N—NO$_3$ with 100 µM calcein and incubated in the dark at room temperature for 20 min to allow for recovery. After recovery, 200 µL of the sonoporated culture was transferred to a sterile microcentrifuge tube, and a 1 mg/mL solution of propidium iodide (PI) was added to the culture at a final concentration of 0.1 mg/mL. After dark incubation at room temperature for 20 min, the culture was diluted 10× or 100× with PBS buffer and run on an Accuri C6 flow cytometer (10,000 events in gated population and a medium flowrate of 35 µL/min). Calcein (Ex/Em=495/515) uptake was measured by fluorescence from the FL1-A channel (Em=533/30), and cell viability from PI (Ex/Em=535/617) staining was measured from the FL2-A channel (Em=585/40). Flow cytometry data were analyzed using FlowJo v10 to quantify uptake of calcein in the live cell population.

For sonoporation with DNA, linearized DNA (1 µg) was added to the prepared cell mixture. The SAW device was operated under the aforementioned conditions with varying power and duration. The sonoporated culture was transferred to 10 mL of F2N—NO$_3$ medium in a conical centrifuge tube and incubated under standard growth conditions with cheesecloth covering the tubes to reduce the light intensity. After 24 hours of recovery, the sonoporated cultures were centrifuged at 3,900×g for 10 min at room temperature and spread onto F2N—NO$_3$ agar plates containing either zeocin (3 µg/mL) or hygromycin (300 µg/mL) for selection at 1× and 10× dilutions with final volumes of 100 µL. Transfection plates were incubated at 25° C. and 100 µE of illumination from cool white and plant fluorescent lights. Resistant colonies were typically observed at 2 weeks, and single colonies were re-streaked on selection plates at approximately 3 weeks.

Electroporation: Electroporation of *N. oceanica* and *N. gaditana* followed a previously published protocol (see, e.g., Kilian O et al., "High-efficiency homologous recombination in the oil-producing alga *Nannochloropsis* sp.," *Proc. Nat'l Acad. Sci.* USA 2011; 108(52):21265-9; and U.S. Pat. No. 8,119,859). In particular, cultures of *N. gaditana* CCMP 526 and *N. oceanica* CCMP 1779 were grown until cell densities reached 5×10$^6$ cells/mL (OD$_{750}$~0.2) or 1×10$^7$ cells/mL (OD$_{750}$~0.4). Culture volumes equivalent to 1×10$^8$ cells were harvested by centrifugation at 3,900×g for 10 min at room temperature in a Beckman Coulter Allegra X-30R centrifuge using conical centrifuge tubes. The supernatant was discarded, and cell pellets were washed with 50 mL of filter-sterilized 375 mM sorbitol solution. The cell pellet was collected by centrifugation at 3,200×g for 10 min at room temperature, and the 50 mL wash procedure was repeated for a total of 4×50 mL washes. The cell pellet was then resuspended in 1 mL of filter-sterilized 375 mM sorbitol solution and transferred to a microcentrifuge tube. The cell pellet was collected by centrifugation at 3,200×g for 5 min at room temperature in an Eppendorf 5424 microcentrifuge, and the supernatant was removed with a pipette. A total of 5×1 mL sorbitol washes was applied to each cell pellet.

After the fifth wash, the cell pellet was resuspended to a final volume of 100 µL using the 375 mM sorbitol solution. Linearized DNA (1 µg in ultrapure water) was added to the dense culture, and the mixture was transferred to a sterile 0.2 cm electroporation cuvette (Bio-Rad). Each cuvette was electroporated using a Bio-Rad Gene Pulser XCell electroporation system, under the following conditions: voltage=2200 V, resistance=500Ω, and capacitance=50 µF, resulting in time constants of 20-23 msec.

The electroporated cultures were resuspended in 10 mL of F2N—NO$_3$ medium in a 15 mL conical centrifuge tube and placed under the aforementioned growth conditions with a cheesecloth covering the tubes. After 24 hours of recovery, the cultures were centrifuged at 3,900×g for 10 min at room temperature, resuspended to a final volume of approximately 200 µL and spread onto F2N—NO$_3$ agar plates containing either zeocin (3 µg/mL) or hygromycin (300 µg/mL) for selection at 1×, 10×, and 100× dilutions with final volumes of 100 μL. Transfection plates were incubated at 25° C. and 100 μE of illumination from cool white and plant fluorescent lights. Resistant colonies were typically observed at 2 weeks, and single colonies were re-streaked on selection plates at approximately 3 weeks.

Confirmation of transfection: Transfection efficiencies were measured by counting colony forming units (cfus), multiplying by the dilution, and dividing by the amount of DNA used in the transfection. After two rounds of re-streaking on selection plates, the transfection candidates were screened for insertion of the ypet or ble genes contained in the transfection plasmids. Cells were scraped from the selection plates and resuspended in 10 μL of 6% Chelex-100 solution, as described previously (see, e.g., Wan M et al., "An improved colony PCR procedure for genetic screening of Chlorella and related microalgae," Biotechol. Lett. 2011; 33(8):1615-9). The 6% Chelex-100 solution was vortexed prior to aliquoting in PCR tubes to ensure homogenous suspension of the Chelex-100 resin. The resuspended cultures were heated at 100° C. for 10 min followed by cooling to 4° C. The lysed cultures were centrifuged at 10,000×g for 1 min to remove cell debris and the Chelex-100 resin. Supernatant (1 μL) was used as template in a PCR reaction to screen for ypet or ble. Taq DNA polymerase (New England Biolabs) was used for screening following the manufacturer's instructions.

Other Embodiments

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

The invention claimed is:

1. A method of transforming a cell, the method comprising:
introducing a cell and an agent into at least one channel of an acoustic cell system comprising an acoustic transducer, wherein the acoustic transducer is configured to be disposed beneath the at least one channel and is adapted to propagate an acoustic wave in the at least one channel;
providing a radiofrequency signal to the acoustic transducer, thereby propagating the acoustic wave and generating localized acoustic pressure in proximity to the cell; and
delivering the agent into the cell, thereby transforming the cell;
wherein the acoustic cell system comprises a surface acoustic wave system or a bulk acoustic wave system;
wherein the cell comprises an algal cell;
wherein the introducing step is conducted in the presence of a nutrient medium;
wherein the nutrient medium has a salinity of from about 3% to about 30%.

2. The method of claim 1, wherein the algal cell is *Nannochloropsis*.

3. The method of claim 1, wherein the agent comprises a nucleic acid.

4. The method of claim 3, wherein the nucleic acid is an expression cassette.

5. The method of claim 1, wherein the nutrient medium has a salinity of from about 3% to about 5%.

6. The method of claim 1, wherein the introducing step comprises flowing the cell and/or the agent into the at least one channel.

7. The method of claim 1, wherein an operating frequency of the acoustic transducer is 10 MHz to 120 MHz.

8. The method of claim 1, wherein a power delivered to the at least one channel is 10 mW to 40 mW.

9. The method of claim 1, wherein the providing step is conducted from about 15 seconds to about 2 minutes.

10. The method of claim 1, wherein the providing step comprises:
generating an acoustic signal with a signal generator electrically connected to the acoustic transducer; and
tuning a frequency of the acoustic signal until a change in surface tension is present within the at least one channel.

11. The method of claim 1, wherein the acoustic cell system comprises:
a cartridge comprising a channel configured to receive one or more test samples comprising the cell;
a platform comprising the acoustic transducer, wherein the acoustic transducer is configured to be coupled reversibly to the cartridge; and
a thermal exchange layer configured to be disposed between the cartridge and the transducer.

12. The method of claim 11, wherein the platform comprises a transducer substrate comprising an electrode configured to be electrically connected to the acoustic transducer; and a radiofrequency driver board comprising one or more contact pads configured to be electrically connected to the electrode.

13. The method of claim 12, wherein the platform further comprises a radiofrequency circuit configured to provide a radiofrequency signal to the driver board.

14. The method of claim 1, wherein the acoustic cell system comprises:
a cartridge comprising a plurality of channels, wherein each channel is configured to receive one or more test samples comprising the cell;
a platform comprising a transducer array, which comprises a plurality of acoustic transducers, wherein the transducer array is configured to be coupled reversibly to the cartridge and wherein each acoustic transducer is configured to be disposed beneath each channel and is adapted to propagate an acoustic wave in the channel, thereby generating the localized acoustic pressure; and
a thermal exchange layer configured to be disposed between the cartridge and the transducer array.

15. The method of claim 14, wherein the platform comprises a transducer substrate comprising a plurality of electrodes, and wherein each electrode is electrically connected to each acoustic transducer; and a radiofrequency driver board comprising one or more contact pads configured to be electrically connected to each of the plurality of electrodes.

16. The method of claim 15, wherein the platform further comprises a radiofrequency circuit configured to provide a radiofrequency signal to the driver board.

17. A method of transforming a cell, the method comprising:
introducing a cell and an agent into at least one channel of an acoustic cell system comprising an acoustic transducer, wherein the acoustic transducer is configured to be disposed beneath the at least one channel and is adapted to propagate an acoustic wave in the at least one channel;

providing a radiofrequency signal to the acoustic transducer, thereby propagating the acoustic wave and generating localized acoustic pressure in proximity to the cell;

delivering the agent into the cell, thereby transforming the cell; and incubating the transformed cell within the at least one channel or within a storage chamber in fluidic communication with the at least one channel;

wherein the acoustic transducer is bulk acoustic wave (BAW) transducer or a surface acoustic wave (SAW) transducer;

wherein the cell comprises an algal cell;

wherein the introducing step is conducted in the presence of a nutrient medium;

wherein the nutrient medium has a salinity of from about 3% to about 30%.

18. The method of claim 6, wherein a transducing substrate and electrodes are configured to provide longitudinal waves through the at least one channel that are perpendicular to a direction of flowing.

19. The method of claim 17, wherein the algal cell is selected from the group consisting of: *Achnanthes, Ankistrodesmus, Aphanizomenon, Arthrospira*, Bacillariophyceae, *Botryococcus, Chlamydocapsa, Chlamydomonas, Chlorella, chlorococcum, Chlorogloeopsis, Chlorophyceae, Chrysophyceae, Dunaliella, Ellipsoidion, Haematococcus, Isochrysis, Kirchneriella, Nannochloropsis, Neochloris, Nitzschia, Ostreococcus, Phaeodactylum, Porphyridium, Pyrmnesium, Scenedesmus, Schizochytrium, Skeletonema, Spirogyra, Spirulina, Synechococcus, Tetraselmis*, and *Thalassiosira*, and combinations thereof.

* * * * *